US008541398B2

(12) United States Patent
Wallace et al.

(10) Patent No.: US 8,541,398 B2
(45) Date of Patent: Sep. 24, 2013

(54) HYDROGEN SULFIDE DERIVATIVES OF NON-STEROIDAL ANTI-INFLAMMATORY DRUGS

(75) Inventors: John L. Wallace, Cochrane (CA); Giuseppe Cirino, Naples (IT); Vincenzo Santagada, Cosenza (IT); Giuseppe Caliendo, Naples (IT)

(73) Assignee: Antibe Therapeutics Inc., Calgary (CA)

( * ) Notice: Subject to any disclaimer, the term of this patent is extended or adjusted under 35 U.S.C. 154(b) by 527 days.

(21) Appl. No.: 12/704,412

(22) Filed: Feb. 11, 2010

(65) Prior Publication Data

US 2010/0210607 A1    Aug. 19, 2010

Related U.S. Application Data

(63) Continuation of application No. 11/779,849, filed on Jul. 18, 2007, now Pat. No. 7,741,359, which is a continuation-in-part of application No. PCT/CA2006/000484, filed on Mar. 31, 2006.

(60) Provisional application No. 60/807,639, filed on Jul. 18, 2006, provisional application No. 60/887,188, filed on Jan. 30, 2007.

(30) Foreign Application Priority Data

May 27, 2005    (WO) ................ PCT/CA2005/000819

(51) Int. Cl.
*A61K 31/603*    (2006.01)
*A61K 31/606*    (2006.01)
*C07D 209/04*    (2006.01)
*C07C 69/76*    (2006.01)

(52) U.S. Cl.
USPC ............. 514/161; 514/162; 548/500; 560/52; 560/85; 560/102; 560/106

(58) Field of Classification Search
USPC .................. 514/161, 162; 548/500; 560/52, 560/85, 102, 106
See application file for complete search history.

(56) References Cited

U.S. PATENT DOCUMENTS

| | | | |
|---|---|---|---|
| 3,338,913 A | 8/1967 | Yates | |
| 4,112,095 A | 9/1978 | Allen, Jr. et al. | |
| 4,170,654 A | 10/1979 | Stone | |
| 4,412,992 A | 11/1983 | Chan | |
| 4,440,763 A | 4/1984 | Lover | |
| 5,013,727 A | 5/1991 | Halskov | |
| 5,214,191 A | 5/1993 | Kirschenheuter et al. | |
| 5,663,416 A | 9/1997 | Kirschenheuter et al. | |
| 5,811,425 A | 9/1998 | Woods et al. | |
| 6,197,341 B1 | 3/2001 | Friess et al. | |
| 6,297,260 B1 | 10/2001 | Bandarage et al. | |
| 6,429,223 B1 | 8/2002 | Lai et al. | |
| 6,458,776 B1 | 10/2002 | Ekwuribe et al. | |
| 6,602,915 B2 | 8/2003 | Uhrich | |
| 7,498,355 B2 * | 3/2009 | Wallace et al. | 514/441 |
| 7,638,513 B2 | 12/2009 | Siddiqui et al. | |
| 7,741,359 B2 * | 6/2010 | Wallace et al. | 514/414 |
| 7,910,568 B2 * | 3/2011 | Wallace et al. | 514/97 |
| 8,114,858 B2 * | 2/2012 | Wallace et al. | 514/166 |
| 2005/0215487 A1 | 9/2005 | Holick et al. | |
| 2006/0270635 A1 | 11/2006 | Wallace et al. | |
| 2008/0020997 A1 | 1/2008 | Capomacchia et al. | |

FOREIGN PATENT DOCUMENTS

| | | |
|---|---|---|
| CA | 2204747 | 3/1997 |
| EP | 1630164 | 3/2006 |
| EP | 1645288 | 4/2006 |
| WO | 99/42439 | 8/1999 |
| WO | 0162085 | 8/2001 |
| WO | WO 2006/037623 | 4/2006 |
| WO | WO 2006/066894 | 6/2006 |
| WO | 2006/100254 | 9/2006 |
| WO | WO 2006/111791 | 10/2006 |
| WO | 2006125293 | 11/2006 |
| WO | WO 2006/125295 | 11/2006 |
| WO | WO 2006/134489 | 12/2006 |
| WO | WO 2007/101606 | 9/2007 |

OTHER PUBLICATIONS

Wallace, J.L. Nonsteroidal anti-inflammatory drugs and gastroenteropathy: the second hundred years. Gastroenterology. 1997; 112:1000-1016.
Grosser et al., Biological basis for the cardiovascular consequences of COX-2 inhibition: therapeutic challenges and opportunities. J Clin Invest. 2006; 116: 4-15.
Wang, Two's company, three's a crowd: can H2S be the third endogenous gaseous transmitter? FASEB J 2002; 16: 1792-1798.
Fiorucci et al., Inhibition of hydrogen sulfide generation contributes to gastric injury caused by anti-inflammatory nonsteroidal drugs. Gastroenterology. 2005; 129: 1210-1224.
Wallace et al., Cyclooxygenase 1 contributes to inflammatory responses in rats and mice: implications for gastrointestinal toxicity. Gastroenterology 1998; 115: 101-109.
Wallace et al., Limited anti-inflammatory efficacy of cyclo-oxygenase-2 inhibition in carrageenan-airpouch inflammation. Br J Pharmacol 1999; 126:1200-1204.
Zanardo et al., Hydrogen sulphide is an endogenous modulator of leukocyte-mediated inflammation. FASEB J 2006; 20: 2118-2120.
Stadler et al., Diclofenac delays healing of gastroduodenal mucosal lesions. Double-blind, placebo-controlled endoscopic study in healthy volunteers. Digestive Diseases and Sciences 1991; 36: 594-600.
Elliott et al., A nitric oxide-releasing nonsteroidal anti-inflammatory drug accelerates gastric ulcer healing in rats. Gastroenterology 1995; 109: 524-530.

(Continued)

*Primary Examiner* — Samantha Shterengarts
(74) *Attorney, Agent, or Firm* — Bennett Jones LLP

(57) ABSTRACT

The present invention relates to derivatives of non-steroidal anti-inflammatory drugs (NSAIDs) having improved anti-inflammatory properties useful in the treatment of inflammation, pain and fever. More particularly, NSAIDs are derivatized with a hydrogen sulfide (H₂S) releasing moiety to produce novel anti-inflammatory compounds having reduced side effects.

18 Claims, 16 Drawing Sheets

(56) References Cited

OTHER PUBLICATIONS

Whelton, A. Nephrotoxicity of nonsteroidal anti-inflammatory drugs: physiologic foundations and clinical implications. Am. J. Med. 1999; 106 (5B): 13S-24S.

Ribeiro et al. (Chronic inhibition of nitric oxide synthesis: A new model or arterial hypertension. Hypertension 1992; 20: 298-303.

Ubuka, T. T Assay methods and biological roles of labile sulfur in animal tissues. J Chromatogr B Analyt Technol Biomed Life Sci. 2002, 781: 227-249.

Zhao W, Zhang J, Lu Y, Wang R. The vasorelaxant effect of H2S as a novel endogenous gaseous K(ATP) channel opener. EMBO J. 2001; 20: 6008-6016.

Dzierzewicz, et al., Susceptibility of Desulfovibrio desulfuricans intestinal strains to sulfasalazine and its biotransformation products, Med. Sci. Monit., 2004, vol. 10, No. 6, BR185-190.

Edmond, et al., The effect of 5-aminosalicylic acid-containing drugs on sulfide production by sulfate-reducing bacteria and amino acid-fermenting bacteria, Inflammatory Bowel Diseases, 2003, vol. 9, No. 1, pp. 10-17.

Distrutti, et al., Evidence that Hydrogen Sulfide exerts Antinociceptive Effects in the Gastrointestinal Tract by Activating KATP Channels, J. Pharmacology & Exp. Ther, Web Release on Sep. 25, 2005, vol. 316, No. 1, pp. 325-335.

Sidhu, et al., L-Cystein and Sodium Hydrogensulfide Inhibit Spontaneous Contractibility in Isolated Pregnant Rat Uterine Strips In Vivo, Pharmacology & Toxicology, 2001, vol. 88, pp. 198-203.

Zhao, et al., The vasorelaxant effect of H2S as a novel endogenous gaseous KATP channel opener, EMBO Journal, 2001, vol. 20, No. 21, pp. 6008-6016.

Zhao, et al., h2S-induced vasorelaxation and underlying cellular and molecular mechanisms, A. J. Physiol. Heart Circ. Physiol., 2002, vol. 283: H474-480.

Teague, et al., "The Smooth Muscle Relaxant Effect of Hydrogen Sulfide In Vitro: Evidence for a Physiological Role to Control Intestinal Contractility", Br. J. Pharmacol, vol. 137, pp. 139-145, 2002.

Abe, et al., "The possible role of hydrogen sulfide as an endogenous neuromodulator", The Journal of Neuroscience, 1996, vol. 16, No. 3, pp. 1066-1071.

Carceller, et al., "Novel Azo derivatives as prodrugs of 5-aminosalicylic acid and amino derivatives with potent platelet activating factor antagonist activity", J. Med. Chem., 2001, vol. 44, No. 18, pp. 3001-3013.

Pellicciari, et al., Brush-Border-Enzyme-Mediated Intestine-Specific Drug Delivery. Amino acid Prodrugs of 5-Aminosalicylic acid, J. Med. Chem. 1993, vol. 36, pp. 4201-4207.

Li et al., "Anti-inflammatory and gastrointestinal effects of a novel diclofenac derivative", Free radical Biology & Medicine, vol. 42, No. 5, Mar. 1, 2007, p. 706-719.

Kourounakis et al., "Reduction of gastrointestinal toxicity of NSAIDs via molecular modifications leading to antioxidant anti-inflammatory drugs", Toxicology (2000) vol. 144, No. 1-3, p. 205-210.

Galankis et al., "Synthesis and pharmacological evaluation of amide conjugates of NSAIDs with L-cysteine ethyl ester, combining potent antiinflammatory and antioxidant properties with significantly reduced gastrointestinal toxicity", Bioorganic & Medicinal Chemistry Letters, vol. 14 (2004), p. 3639-3643.

Bhatia et al., "Treatment with H2S-releasing derivative of diclofenac reduces inflammation in carrageenan-induced hindpaw oedema", Inflammation Research, Suppl.2, 7th World Congress on Inflammation, Aug. 20-24, 2005, Melbourne, Australia.

Szabo et al., "Protection against aspirin-induced hemorrhagic erosions and mucosal vascular injury by co-administration of sulfhydryl drugs", Gastroenterology (1985), vol. 88, No. 5 Part 2, p. 1604.

Fiorucci et al., "The emerging roles of hydrogen sulfide in the gastrointestinal tract and liver", Gastroenterology, Jul. 2006, vol. 131, No. 1, p. 259-271.

Fiorucci et al., Enhanced activity of hydrogen sulphide-releasing derivative of mesalamine (ATB-429) in a mouse model of colitis, British Journal of Pharmacology (2007), 150, 996-1002.

Distrutti et al., "5-Amino-2hydroxybenzoic Acid 4-(5-Thioxo-5H-[1,2]dithiol03y1)-phenyl Ester (ATB-429), a Hydrogen Sulfide-Releasing Derivative of Mesalamine, Exerts Antinociceptive Effects in a Model of Postinflammatory Hypersensitivity", The Journal of Pharmacology and Experimental Therapeutics 2006, vol. 319 No. 1, 447-458.

Schicho et al., "Hydrogen Sulfide is a Novel Prosecretory Neuromodulator in the Guinea-Pig and Human Colon", Gastroenterology 2006, 131:1542-1552.

Wallace et al., "Gastrointestinal Safety and Anti-Inflammatory Effects of a Hydrogen Sulfide-Releasing Diclofenac Derivative in the Rat", Gastroenterology 2007, 132:261-271.

Isenberg et al., "Modulation of angiogenesis by dithiolethione-modified NDAIDs and valproic acid", British Journal of Pharmacology (2007) 151, 142-151.

Ling et al., "Anti Inflammatory activity of S-diclofenac, a novel H2S -releasing diclofenac derivative", Abstracts, The 15th World Congress of Pharmacology, Jul. 2-7, 2006, P260055, pp. 270.

Kartasasmita, Rahmana E. et al: "NO-donors (VII (1)) : Synthesis and cyclooxygenase inhibitory properties of N- and S-nitrooxypivaloyl-cysteine derivatives of naproxen: A novel type of NO-NSAID." Archiv Der Pharmazie (Weinheim), vol. 335, No. 8, Oct. 2002, pp. 363-366, XP002366914 ISSN: 0365-6233.

Gyires, Klara: "Some of the factors that amy mediate or modify the gastrointestinal mucosal damage induced by non-steroidal anti-inflammatory drugs" Agents and Actions, vol. 41, No. 1-2, 1994, pp. 73-79, XP009061171 ISSN: 0065-4299.

Ueshima, K. et al.: "Effects of Sulfhydryl-related compounds on indomethacin-induced gastric lesions in rats role of endogenous sulfhydryls in the pathogenesis" Japanese Journal of Pharmacology, vol. 58, No. 2, 1992, pp. 157-165, XP009061173 ISSN: 021-5198.

Balint, G A et al.: "The effect of D Penicillamine in different experimental gastric ulcer models in teh rat" Acta Medica Hungarica, vol. 42, No. 3-4, 1985, pp. 175-178, XP009061170 ISSN: 0236-5286.

Szabo, S et al.: "Sulfhydryl drugs a new type of gastric cytoprotective agent" Gastroenterology, vol. 80, No. 5 Part 2, 1981, p. 1298, XP009061172 & Digestive Disease Week and the 82nd Annual Meeting of the American Gastroenterological Associateion, ISSN:0016-5085.

Christen, M-O: "Anethole Dithiolethione: Biochemical considerations" Methods in Enzymology, Academic Press Inc., San Diego, CA, US, vol. 252, 1995, pp. 316-323, XP008048195 ISSN: 0076-6879.

Van Boi et al., Chemical Abstracts, 132:293322, 2000.

Wang, G.W. et al. Novel Reactions of [60]Fullerene with Amino Acid Esters and Carbon Disulfide. J. Org. Chem. 2006. pp. 680-684. vol. 71.

Molin, J. et al. On Mechanism of Base-Catalysed Hydrolysis of Thioamides. Collection Czechoslov. Chem. Commun. 1977. pp. 517-523. vol. 42.

Molin, J. et al. Substituent and Solvent Effects in Alkaline Hydrolysis of Thioamides. Collection Czechoslov. Chem. Commun. 1978. pp. 2283-2288. vol. 43.

Fiorucci, S. et al. A New Protective Mechanism in NSAID Gastropathy. Evidence That Hydrogen Sulfide (h2s) Modulates Gastric Mucosal Integrity. Annual Meeting of American Gastroenterological Association. 2005. Abstract No. 836.

\* cited by examiner

HYDROGEN SULFIDE DERIVATIVES OF NON-STEROIDAL ANTI-INFLAMMATORY DRUGS

This application is filed as a Continuation-in-Part of PCT/CA2006/000484, filed Mar. 31, 2006, which claims priority to PCT/CA2005/000819, filed May 27, 2005. This application further claims priority to U.S. provisional patent applications Nos. 60/807,639, filed Jul. 18, 2006, and 60/887,188, filed Jan. 30, 2007.

FIELD OF INVENTION

The present invention relates to derivatives of non-steroidal anti-inflammatory drugs (NSAIDs) having improved anti-inflammatory properties useful in the treatment of inflammation, pain and fever. More particularly, NSAIDs are derivatized with a hydrogen sulfide ($H_2S$) releasing moiety to produce novel anti-inflammatory compounds having reduced side effects.

BACKGROUND OF THE INVENTION

Non-steroidal anti-inflammatory drugs (NSAIDs) are widely used for the treatment of a variety of conditions associated with pain, fever and inflammation, including osteoarthritis, rheumatoid arthritis, gout and ankylosing spondylitis. They are also widely used for treating acute pain associated with injuries and surgical procedures (including dental procedures) and headaches. The beneficial effects of NSAIDs are largely believed to be attributable to their ability to suppress prostaglandin synthesis by inhibiting cyclooxygenase-1 (COX-1) and cyclooxygenase-2 (COX-2).

However, long-term use of NSAIDs is significantly limited by their ability to cause clinically significant injury in the gastrointestinal tract (Wallace, J. L. Nonsteroidal anti-inflammatory drugs and gastroenteropathy: the second hundred years. *Gastroenterology.* 1997; 112:1000-1016). Selective inhibitors of COX-2 were seen as an advance on conventional NSAIDs, as they appeared to cause less gastrointestinal injury. However, concerns have been raised regarding the cardiovascular toxicity these drugs, and possibly also regarding conventional NSAIDs (Grosser et al., Biological basis for the cardiovascular consequences of COX-2 inhibition: therapeutic challenges and opportunities. *J Clin Invest.* 2006; 116: 4-15).

It is well known that NSAIDs stimulate leukocyte adherence and reduce gastric mucosal blood flow, and these actions are widely held to be important contributors to the pathogenesis of NSAID-induced gastrointestinal damage (Wallace, 1997). Induction of leukocyte adherence by non-selective and COX-2-selective NSAIDs may also contribute to cardiovascular complications of these drugs.

Recently, it has been observed that hydrogen sulfide ($H_2S$) exerts anti-inflammatory and analgesic activities. $H_2S$ is an endogenous substance, produced in many tissues and affecting many functions (Wang, Two's company, three's a crowd: can $H_2S$ be the third endogenous gaseous transmitter? *FASEB J* 2002; 16: 1792-1798). It has also been shown to be a vasodilator and can suppress leukocyte adherence to the vascular endothelium (Wang, 2002; Fiorucci et al., Inhibition of hydrogen sulfide generation contributes to gastric injury caused by anti-inflammatory nonsteroidal drugs. *Gastroenterology.* 2005; 129: 1210-1224). Further, Fiorucci et al. (2005) have demonstrated that pretreatment with an $H_2S$ donor can diminish the severity of NSAID-induced gastric damage in the rat.

Surprisingly, the inventors have shown in the present application that the anti-inflammatory activity of a variety of NSAIDs is significantly enhanced when covalently linked to or NSAID salts are formed with an $H_2S$ releasing moiety. Further, these NSAID derivatives have been shown to have reduced side effects. In particular, the inventors have shown that NSAID derivatives of the present invention have one or more of the following additional characteristics: (1) produce less gastrointestinal injury than conventional NSAIDs; (2) accelerate the healing of pre-existing gastric ulcers; and (3) elicit significantly less of an increase in systemic blood pressure than conventional NSAIDs. Furthermore, the NSAID derivatives of the present invention reduce leukocyte adherence to the vascular endothelium, which may contribute to both reduced gastrointestinal and cardiovascular side effects.

SUMMARY OF THE INVENTION

In one aspect of the present invention, derivatives of NSAIDs are provided, said derivatives comprising an $H_2S$-releasing moiety that is either covalently linked to an NSAID or forms a salt with an NSAID. Surprisingly, the compounds of the present invention exhibit enhanced anti-inflammatory activity in a rat carrageenan-induced paw edema model when compared to the NSAID alone, the $H_2S$-releasing moiety alone, and the combination of NSAID and $H_2S$-releasing moiety administered separately but concomitantly. Furthermore, the NSAID derivatives of the present invention produce a modest, short-lived increase in plasma $H_2S$ concentrations. Without being bound to theory, the short-lived increase in plasma $H_2S$ concentrations, which is still within the physiological range, may contribute to, their enhanced anti-inflammatory activity.

Surprisingly, the compounds of the present invention may also exhibit an enhanced ability to suppress cyclooxygenase-2 (COX-2) activity and/or cyclooxygenase 1 (COX-1) activity when compared to their respective non-derivatized NSAID counterparts. Such an enhanced ability to suppress COX-2 and/or COX-1 may also contribute to the increased anti-inflammatory activity observed. Furthermore, the compounds of the present invention having enhanced inhibition of COX-1 showed a significant suppression of thromboxane $B_2$ production in platelets, which may contribute to reduced cardiovascular toxicity.

Further, the compounds of the present invention exhibit fewer side effects than their respective non-derivatized counterparts. For example, some compounds surprisingly induced significantly less gastric injury than the NSAID alone, despite the compounds markedly suppressing gastric prostaglandin synthesis. While gastric safety is observed with these $H_2S$-releasing derivatives of NSAIDs, the same is not the case if the NSAID and the $H_2S$-releasing moiety are administered separately, but concomitantly to rats. Without being bound to theory, the compounds of the present invention were shown to reduce leukocyte adherence to the vascular endothelium, which may contribute to their gastric safety. Further, reduced leukocyte adherence to the vascular endothelium may reduce the cardiovascular side effects frequently seen with prolonged use of NSAIDs.

Further, the compounds of the present invention surprisingly induced significantly less of an increase in systolic blood pressure when administered to hypertensive rats than was observed when conventional NSAIDs were administered. A reduced propensity to elevate blood pressure may reduce the cardiovascular side effects frequently seen with prolonged use of NSAIDs.

In accordance with the present invention, there are provided compounds having the following general formula:

A-Y—X        (Formula I)

where A is an NSAID radical, Y is selected from the group consisting of —C(O)O—, —C(O)NH—, —C(O)OC(O)—, —C(O)NHCH$_2$C(O)—, or zero, and X is a moiety capable of releasing hydrogen sulfide either alone or when coupled to the NSAID (hereinafter referred to as an H$_2$S-releasing moiety), or a pharmaceutically acceptable salt thereof, whereby when Y is zero, the NSAID derivative may be a salt of A and X.

In a preferred embodiment, X of Formula I is selected from the group consisting of:

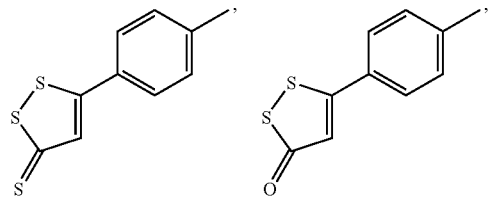

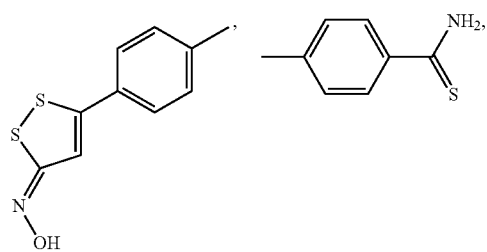

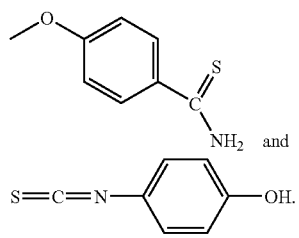

It is understood, however, that any non-toxic, effective moiety capable of releasing H$_2$S, either alone or when coupled to an NSAID, can be used in the present invention.

In one embodiment, compounds of the invention have the following general formula:

B—C(O)O—X        (Formula II)

where B—C(O)O— is derived from an NSAID having a free carboxyl group or a carboxy-substituted NSAID and X is an H$_2$S-releasing moiety, or a pharmaceutically acceptable salt thereof.

In one embodiment, B—C(O)O— of Formula II is selected from the group consisting of:

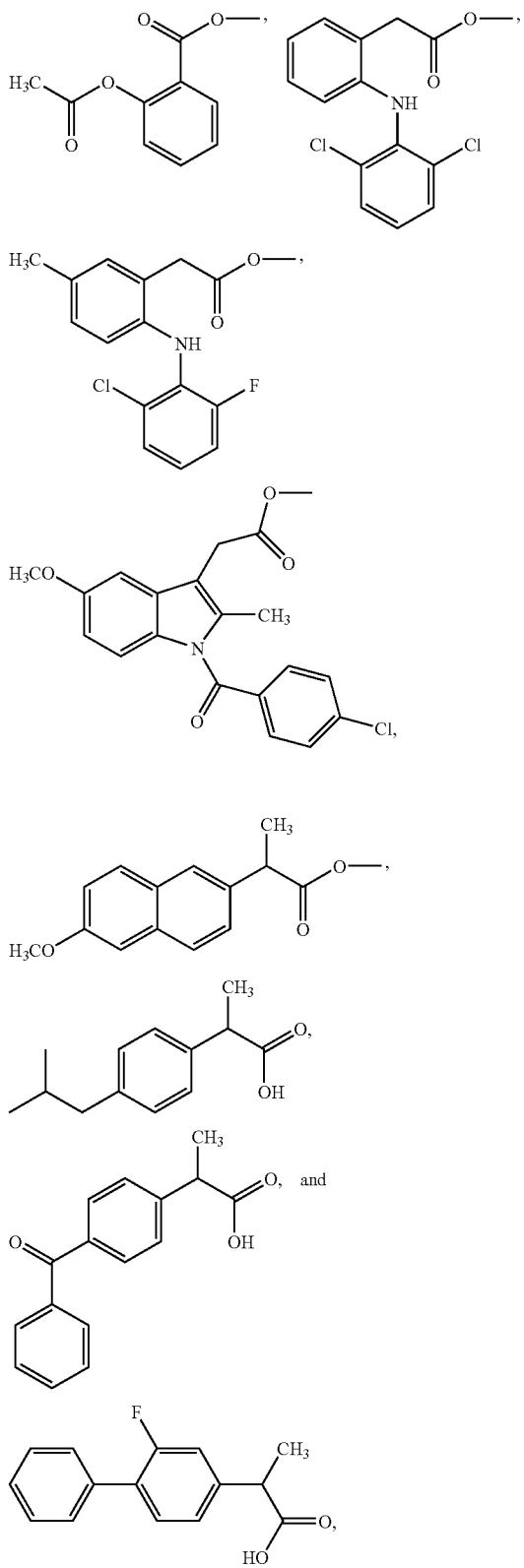

and X is a hydrogen sulfide (H$_2$S) releasing moiety.

In one embodiment, X of Formula II is selected from the group consisting of:

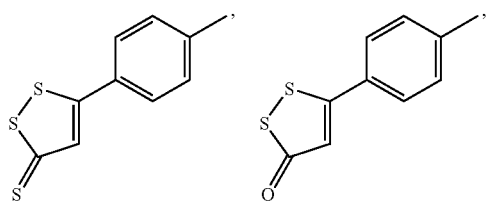

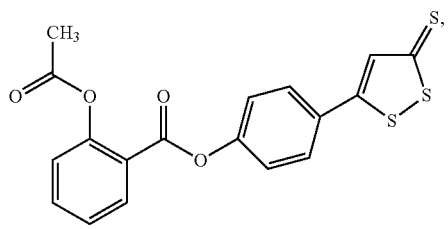

It is understood, however, that any non-toxic, effective moiety capable of releasing H₂S, either alone or when coupled to an NSAID, can be used in the present invention.

NSAIDs contemplated for incorporation in the compounds of the present invention include acetylsalicylic acid (ASA), diclofenac, naproxen, indomethacin, flurbiprofen, sulindac, ibuprofen, aceclofenac, acemetacin, benoxaprofen, benzofenac, bromfenac, bucloxic acid, butibufen, carprofen, celecoxib, cicloprofen, cinmetacin, clidenac, clopirac, diflusinal, etodolac, etoricoxib, fenbufen, fenclofenac, fenclorac, fenoprofen, fentiazac, flunoxaprofen, furaprofen, furobufen, furafenac, ibufenac, indoprofen, isoxepac, ketoprofen, ketorolac, loxoprofen, lonazolac, lumiracoxib, metiazinic, mefenamic acid, meclofenamic acid, meloxicam, nabumetone, piromidic acid, salsalate, miroprofen, oxaprozin, oxepinac, paracoxib, phenylbutazone, pirprofen, piroxicam, pirozolac, protizinic acid, rofecoxib, sodium salicylate, suprofen, tiaprofenic acid, tolmetin, valdecoxib, zomepirac, and the like.

Preferred compounds are those of the following formulae:

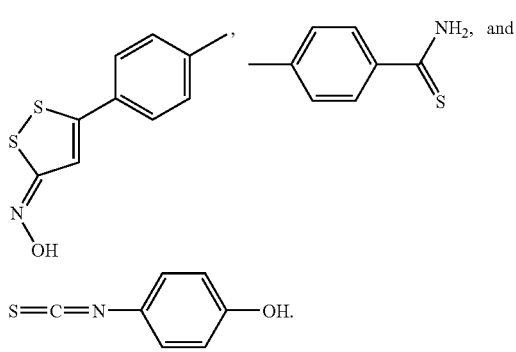

4-(5-thioxo-5H-1,2-dithiol-3-yl)phenyl 2-acetoxybenzoate (I)

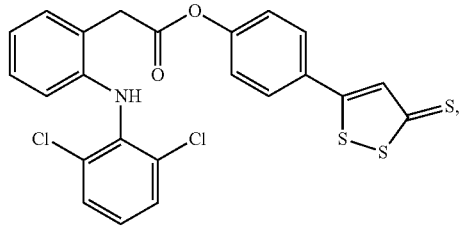

4-(5-thioxo-5H-1,2-dithiol-3-yl)phenyl 2-(2-(2,6-dichlorophenylamino)phenyl)acetate (II)

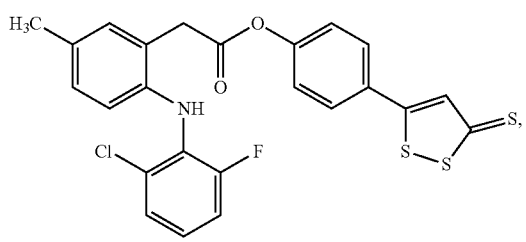

4-(5-thioxo-5H-1,2-dithiol-3-yl)phenyl 2-(2-(2-chloro-6-fluorophenylamino)-5-methylphenyl)acetate (III)

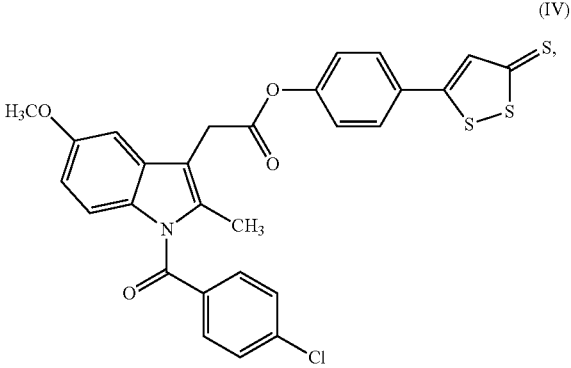

[1-(4-Chloro-benzoyl)-5-methoxy-2-methyl-1H-indol-3-yl]-acetic acid 4-(5-thioxo-5H-[1,2]dithiol-3-yl)-phenyl ester (IV)

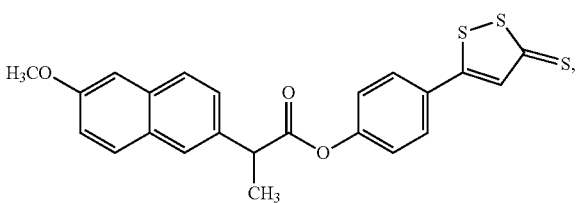

2-(6-Methoxy-naphthalen-2-yl)-propionic acid 4-(5-thioxo-5H-[1,2]dithiol-3-yl)-phenyl ester (V)

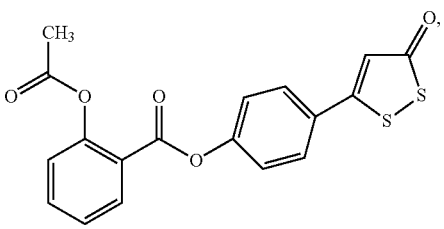

2-Acetoxy-benzoic acid 4-(5-oxo-5H-[1,2]dithiol-3-yl)-phenyl ester (VI)

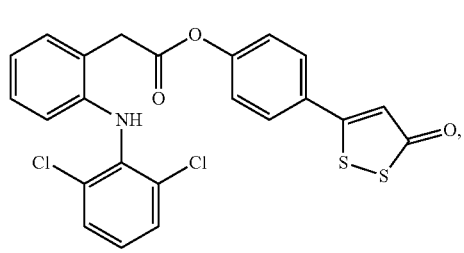

[2-(2,6-Dichloro-phenylamino)-phenyl]-acetic acid 4-(5-oxo-5H-[1,2]dithiol-3-yl)-phenyl ester
(VII)

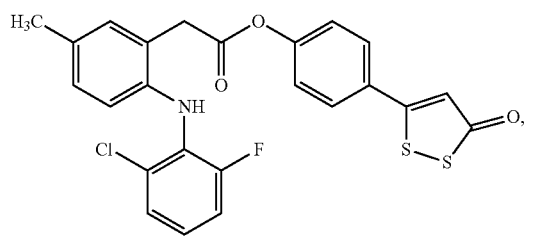

[2-(2-Chloro-6-fluoro-phenylamino)-5-methyl-phenyl]-acetic acid 4-(5-oxo-5H-[1,2]dithiol-3-yl)-phenyl ester
(VIII)

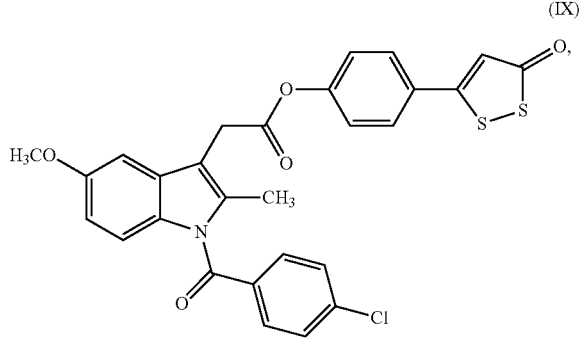

[1-(4-Chloro-benzoyl)-5-methoxy-2-methyl-1H-indol-3-yl]-acetic acid 4-(5-oxo-5H-[1,2]dithiol-3-yl)-phenyl ester
(IX)

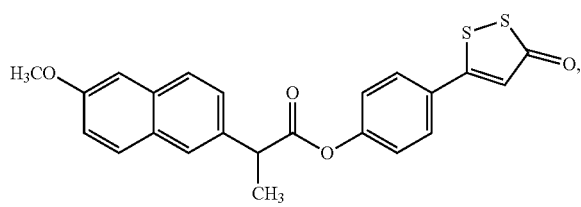

2-(6-Methoxy-naphthalen-2-yl)-propionic acid 4-(5-oxo-5H-[1,2]dithiol-3-yl)-phenyl ester
(X)

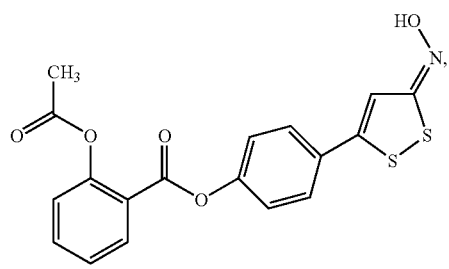

2-Acetoxy-benzoic acid 4-(5-hydroxyimino-5H-[1,2]dithiol-3-yl)-phenyl ester
(XI)

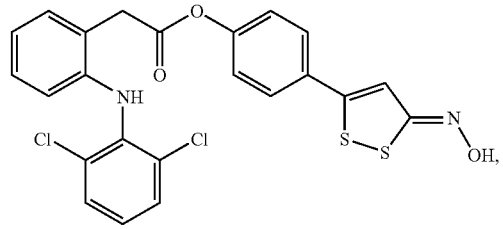

[2-(2,6-Dichloro-phenylamino)-phenyl]-acetic acid 4-(5-hydroxyimino-5H-[1,2]dithiol-3-yl)-phenyl ester
(XII)

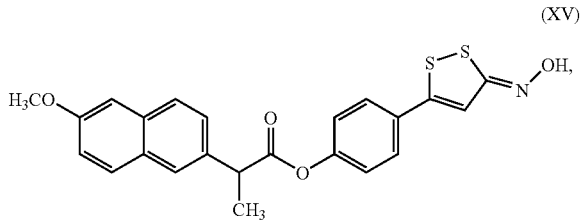

[2-(2-Chloro-6-fluoro-phenylamino)-5-methyl-phenyl]-acetic acid 4-(5-hydroxyimino-5H-[1,2]dithiol-3-yl)-phenyl ester
(XIII)

(XIV)

[1-(4-Chloro-benzoyl)-5-methoxy-2-methyl-1H-indol-3-yl]-acetic acid 4-(5-hydroxyimino-5H-[1,2]dithiol-3-yl)-phenyl ester (XV)

2-(6-Methoxy-naphthalen-2-yl)-propionic acid 4-(5-hydroxyimino-5H-[1,2]dithiol-3-yl)-phenyl ester

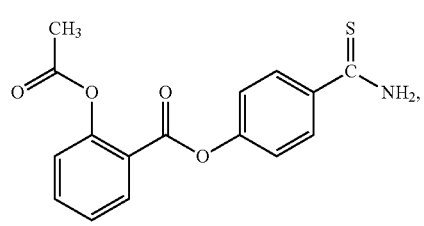

2-Acetoxy-benzoic acid 4-thiocarbamoyl-phenyl ester
(XVI)

(XVII)

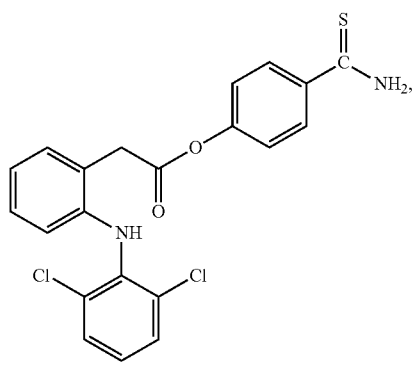

[2-(2,6-Dichloro-phenylamino)-phenyl]-acetic acid 4-thiocarbamoyl-phenyl ester (XVIII)

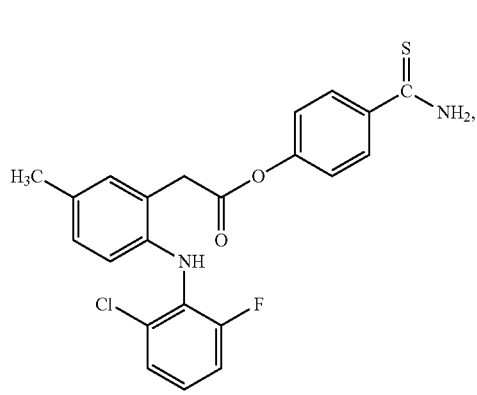

[2-(2-Chloro-6-fluoro-phenylamino)-5-methyl-phenyl]-acetic acid 4-thiocarbamoyl-phenyl ester (XIX)

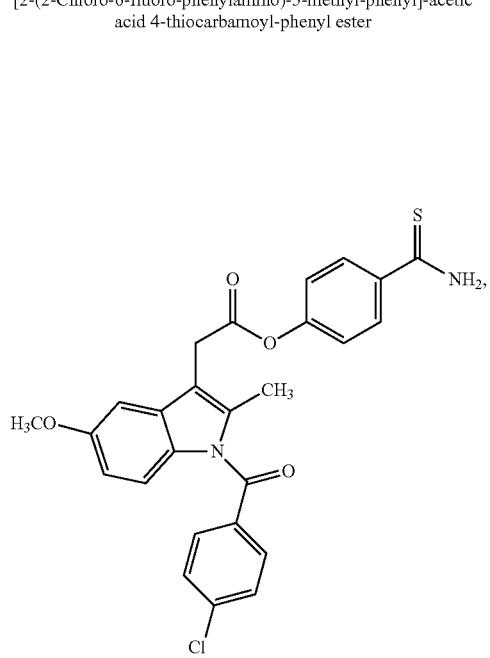

[1-(4-Chloro-benzoyl)-5-methoxy-2-methyl-1H-indol-3-yl]-acetic acid 4-thiocarbamoyl-phenyl ester (XX)

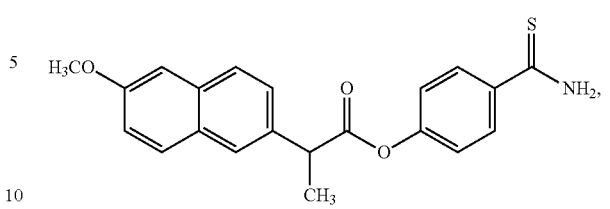

2-(6-Methoxy-naphthalen-2-yl)-propionic acid 4-thiocarbamoyl-phenyl ester (XXI)

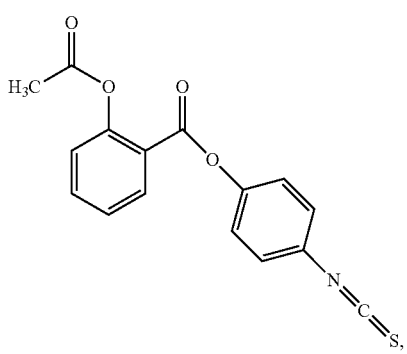

4-isothiocyanatophenyl 2-acetoxybenzoate (XXII)

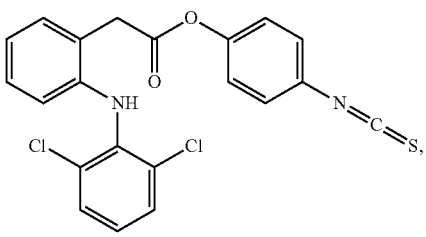

4-isothiocyanatophenyl 2-(2-(2,6-dichlorophenylamino)phenyl)acetate (XXIII)

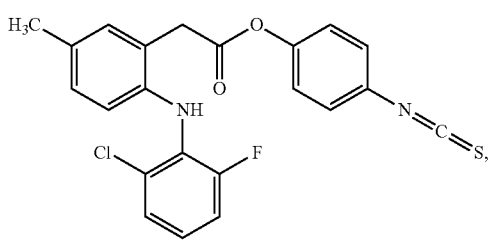

4-isothiocyanatophenyl 2-(2-(2-chloro-6-fluorophenylamino)-5-methylphenyl)acetate

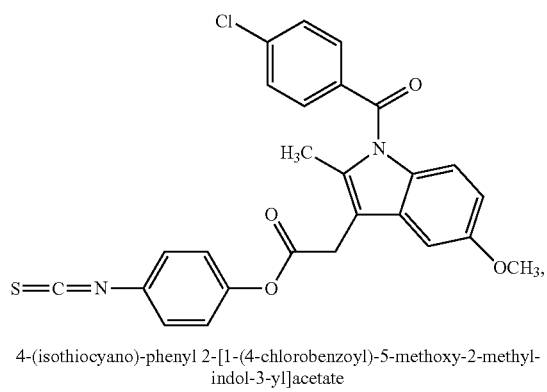

4-(isothiocyano)-phenyl 2-[1-(4-chlorobenzoyl)-5-methoxy-2-methyl-indol-3-yl]acetate (XXXIV)

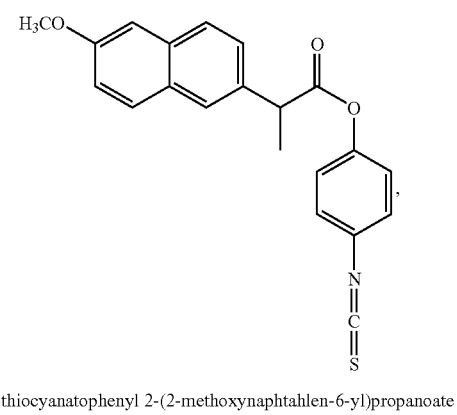

4-isothiocyanatophenyl 2-(2-methoxynaphtahlen-6-yl)propanoate (XXV)

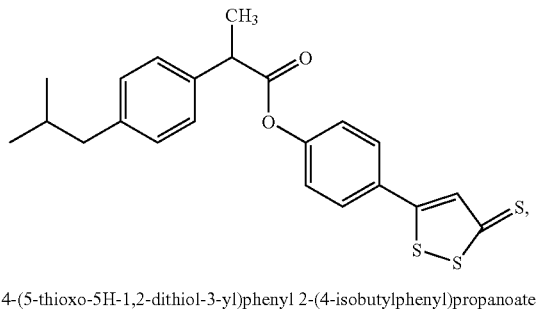

4-(5-thioxo-5H-1,2-dithiol-3-yl)phenyl 2-(4-isobutylphenyl)propanoate (XXVI)

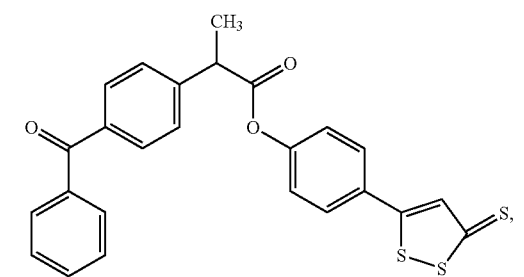

4-(5-thioxo-5H-1,2-dithiol-3-yl)phenyl 2-(3-benzoylphenyl)propanoate (XXVII)

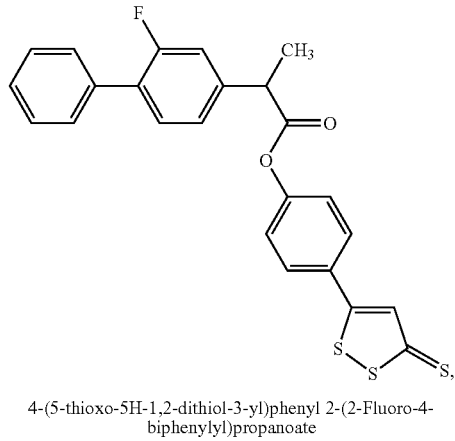

4-(5-thioxo-5H-1,2-dithiol-3-yl)phenyl 2-(2-Fluoro-4-biphenylyl)propanoate (XXVIII)

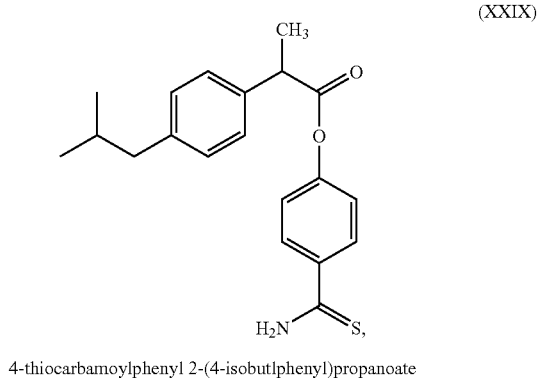

4-thiocarbamoylphenyl 2-(4-isobutlphenyl)propanoate (XXIX)

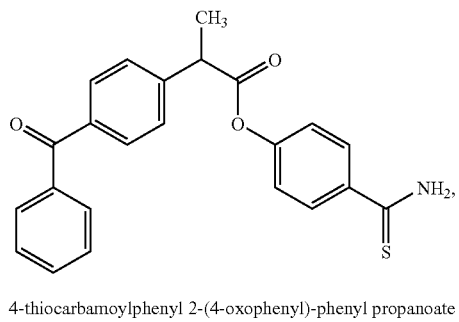

4-thiocarbamoylphenyl 2-(4-oxophenyl)-phenyl propanoate (XXX)

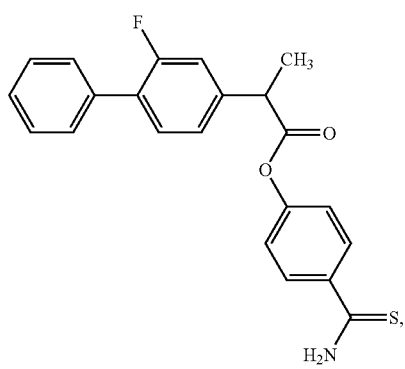

4-thiocarbamoylphenyl 2-(2-Fluoro-4-biphenylyl)propanoate (XXXI)

(XXXII)

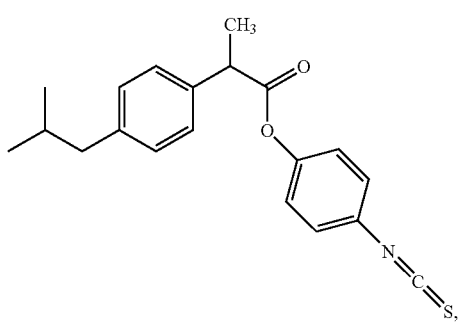

4-isothiocyanatophenyl 2-(4-isobutlphenyl)propanoate (XXXIII)

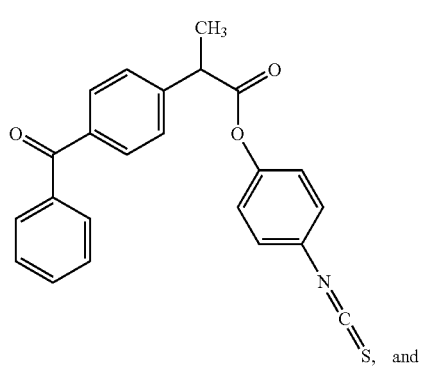

4-(isothiocyano)-phenyl 2-(4-oxophenyl)-phenyl propanoate (XXXIV)

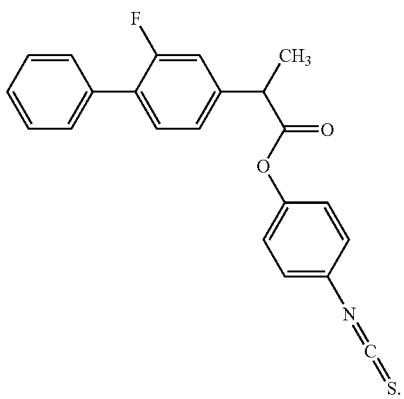

4-(isothiocyano)-phenyl 2-(2-Fluoro-4-biphenylyl)propanoate

The above mentioned precursor NSAIDs (A) are prepared according to the methods known in the prior art. See, for example, The Merck Index, 13th Edition (2001), Merck & Co., Whitehouse Station, N. J., incorporated herein by reference. When available, the corresponding isomers, comprising optical isomers, can be used.

Pharmaceutical acceptable salts of the compounds of the present invention such as, for example, salts with alkaline metals and alkaline earth metals, non-toxic amines and amino acids are also part of the present invention. Preferred salts of the compounds of the present invention are the salts with arginine and agmatine. Also included are pharmaceutically acceptable acid addition salts.

In a preferred embodiment, the NSAIDs of the present invention are derivatized with the H₂S-releasing moiety 4-hydroxythiobenzamide (referred to herein as TBZ). The TBZ derivatives consistently showed better overall anti-inflammatory activity and reduced side effects when compared to the 5-p-hydroxyphenyl-1,2-dithiole-3-thione (ADT-OH) derivatives. Surprisingly, the TBZ derivatives generated significantly more H₂S than the ADT-OH derivatives, which may contribute to both the increase in anti-inflammatory activity and the reduced side effects.

Further, the TBZ derivatives retained the ability to inhibit COX-1/COX-2 more consistently than the ADT-OH derivatives. In fact, many TBZ derivatives actually showed an increase in COX-1 inhibition or COX-2 inhibition or both. Furthermore, Compound XX (naproxen-TBZ derivative) was significantly better at inhibiting thromboxane B2 synthesis than the ADT-OH equivalent, Compound V (naproxen-ADT-OH), and Compound XIX (indomethacin-TBZ derivative) was significantly better at inhibiting thromboxane B2 synthesis than the ADT-OH equivalent, Compound IV (indomethacin-ADT-OH derivative). Enhanced thromboxane B2 inhibition may contribute to the cardiovascular safety of the present derivatives.

Compounds of the present invention can be prepared as illustrated in the following two schemes:

Scheme 1

Scheme 1 is shown below using as an example the synthesis of 4-(5-thioxo-5H-1,2-dithiol-3-yl)phenyl 2-(2-(2,6-dichlorophenylamino)phenyl acetate (Compound II)

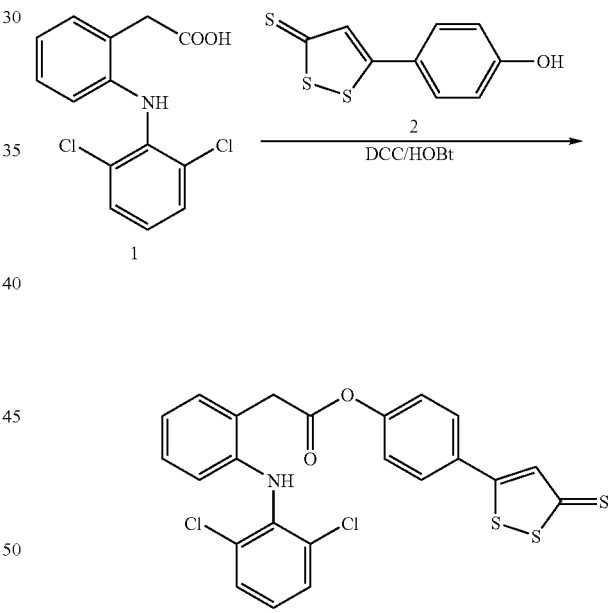

An NSAID having a free carboxyl group (or a carboxy-substituted NSAID), for example, diclofenac (1), is first dissolved in dimethylformamide, and hydroxybenzotriazole (HOBt) and 1,3-dicyclohexylcarbodiimide (DCC) are added. To this mixture is added a hydrogen sulfide-releasing moiety such as 5-p-hydroxyphenyl-1,2-dithiole-3-thione (ADT-OH) (2) under conditions suitable to form invention compounds such as 4-(5-thioxo-5H-1,2-dithiol-3-yl)phenyl 2-(2-(2,6-dichlorophenylamino)phenyl)acetate (3). It is understood that other hydrogen-sulfide releasing moieties can be used with this scheme such as 4-hydroxyphenylisothiocyanate (referred to herein as HPI)

Scheme 2

Scheme 2 is shown below using as an example the synthesis of [2-(2-,6-dichloro-phenylamino)-phenyl]-acetic acid 4-thiocarbamoyl-phenyl ester (Compound XVII). In this scheme, Lawesson reagent is used to add a sulfur group to the hydrogen sulfide releasing moiety after it is covalently bound to the NSAID.

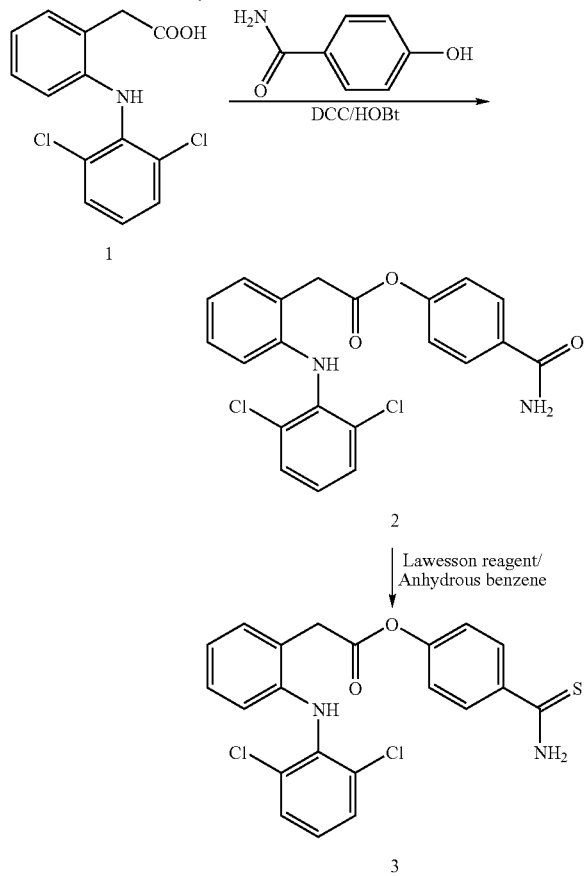

An NSAID having a free carboxyl group (or a carboxy-substituted NSAID), for example, diclofenac (1), is first dissolved in dimethylformamide, and hydroxybenzotriazole (HOBt) and 1,3-dicyclohexylcarbodiimide (DCC) are added. To this mixture is added a hydrogen sulfide-releasing precursor such as 4-hydroxybenzamide under conditions suitable to form a precursor (e.g., 4-carbamoylphenyl 2-(2-(2,6-dichlorophenylamino)phenyl)acetate (2)) of a compound of the present invention, which precursor lacks a sulfur. A suitable compound which can add a sulfur group such as Lawesson reagent is added to form a compound of the present invention (e.g., [2-(2,6-dichloro-phenylamino)-phenyl]-acetic acid 4-thiocarbamoyl-phenyl ester (3).

In a further aspect the present invention provides a pharmaceutical composition of the compounds of the present invention, and a pharmaceutically acceptable excipient or carrier, particularly one for use in the treatment of an inflammatory condition of the GI tract.

Compounds of the present invention would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of the invention would be useful to treat arthritis, including but not limited to rheumatoid arthritis, spondyloarthopathies, gouty arthritis, osteoarthritis, systemic lupus erythematosus and juvenile arthritis. Such compounds of the invention would be useful in the treatment of asthma, bronchitis, menstrual cramps, tendinitis, bursitis, skin-related conditions such as psoriasis, eczema, burns and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis, and for the prevention or treatment of cancer, such as colorectal cancer. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as retinitis, retinopathies, uveitis, ocular photophobia, and of acute injury to the eye tissue. The compounds would also be useful in the treatment of pulmonary inflammation, such as that associated with viral infections and cystic fibrosis. The compounds would also be useful for the treatment or certain central nervous system disorders such as cortical dementias including Alzheimer's disease. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, atherosclerosis and central nervous system damage resulting from stroke, ischemia and trauma. The compounds would also be useful in the treatment of pain, but not limited to postoperative pain, dental pain, muscular pain, and pain resulting from cancer. Besides being useful for human treatment, these compounds are also useful for treatment of mammals, including horses, dogs, cats, rats, mice, sheep, pigs, etc.

Depending on the specific condition or disease state to be treated, subjects may be administered compounds of the present invention at any suitable therapeutically effective and safe dosage, as may be readily determined within the skill of the art. These compounds are, most desirably, administered in dosages ranging from about 1 to about 2000 mg per day, in a single or divided doses, although variations will necessarily occur depending upon the weight and condition of the subject being treated and the particular route of administration chosen. It is understood that dosages will be affected by the particular NSAID used to form the compounds of the present invention. However, a dosage level that is in the range of about 0.1 to about 100 mg/kg, preferably between about 5 and 90 mg/kg, and more preferably between about 5 and 50 mg/kg, is most desirable. Variations may nevertheless occur depending upon the weight and conditions of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such large doses are first divided into several small doses for administration throughout the day.

The compounds of the present invention can be administered in the form of any pharmaceutical formulation, the nature of which will depend upon the route of administration. These pharmaceutical compositions can be prepared by conventional methods, using compatible, pharmaceutically acceptable excipients or vehicles. Examples of such compositions include capsules, tablets, transdermal patches, lozenges, troches, sprays, syrups, powders, granulates, gels, elixirs, suppositories, and the like, for the preparation of extemporaneous solutions, injectable preparations, rectal, nasal, ocular, vaginal etc. A preferred route of administration is the oral and rectal route.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with sweetening or flavoring agents, coloring matter and, if so desired, emulsifying and/or suspending agents, together with such diluents as water, ethanol, propylene glycol, glycerin and various combinations thereof.

The dosage form can be designed for immediate release, controlled release, extended release, delayed release or targeted delayed release. The definitions of these terms are known to those skilled in the art. Furthermore, the dosage form release profile can be effected by a polymeric mixture composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. The aqueous solutions are suitable for intravenous injection purposes. The preparation of all these solutions under sterile conditions is readily accomplished by standard pharmaceutical techniques well known to those skilled in the art.

The following examples further describe and enable a person ordinarily skilled in the art to make and use the invention. It should be appreciated however that these embodiments are for the purpose of illustrating the invention, and are not to be construed as limiting the scope of the invention as defined by the claims.

DETAILED DESCRIPTION OF THE INVENTION

Preparation of Compounds

Figure 1:
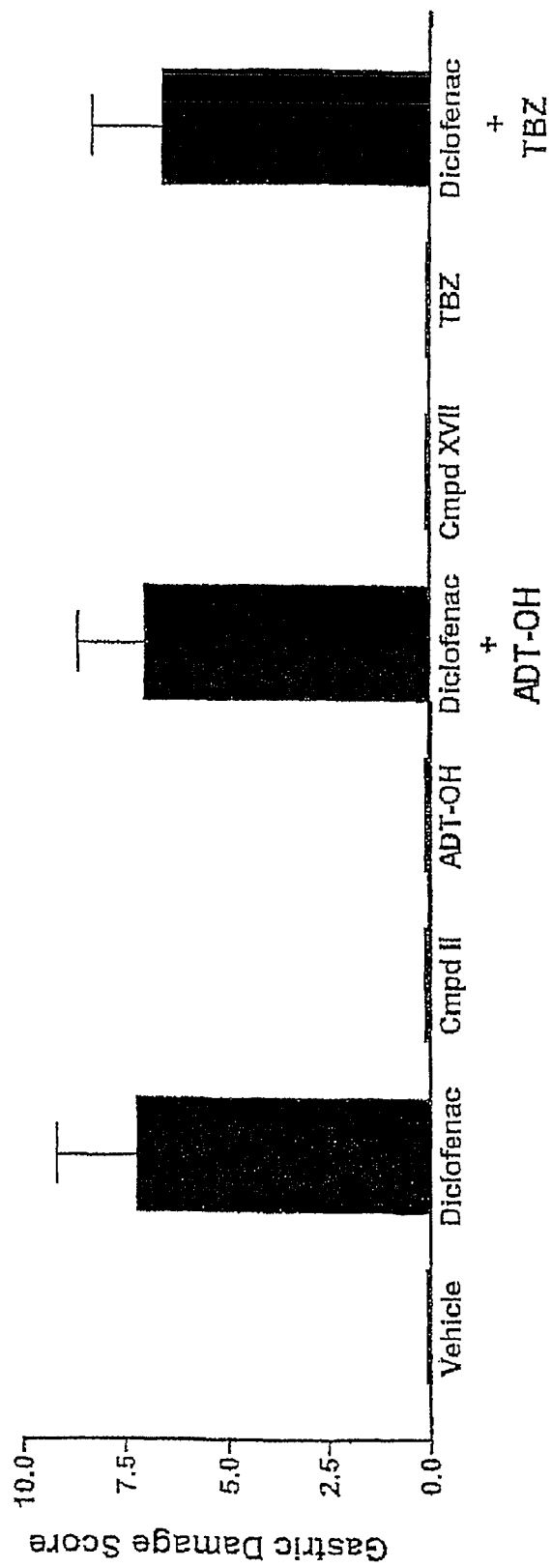
FIG. 1 illustrates the gastric damage score measured in rats treated with vehicle, diclofenac, and two diclofenac derivatives of the present invention, Compound II and Compound XVII.

Thin layer chromatography was performed on Macherey-Nagel silica gel 50 plates with fluorescent indicator and the plates were visualized with UV light (254 nm). Kieselgel 60 was used for column chromatography. All synthetic reagents were purchased from the Aldrich-Sigma Chemical Company and were used without purification. Solvents were analytical reagent grade or higher purity and were used as supplied. A Buchi R-114 rotavapor was utilized for the removal of the solvents in vacuo. The structures were verified spectroscopically by proton $^1$H-NMR and $^{13}$C-NMR. Spectra were recorded on Varian Mercury Plus 400 instrument. Chemical shifts are referred to $Me_4Si$ as internal standard. Mass spectra of the synthesized products were performed on Applied Biosystem API 2000 mass spectrometry. Melting point was performed on Buchi B-540 instrument. The purity of the final compound was determined by RP-HPLC. The column was connected to Rheodyne model 7725 injector, a Waters 600 HPLC system, a Waters 486 tunable absorbance detector set to 215 or 235 nm and a Waters 746 chart recorder. The synthesized compounds gave satisfactory elemental analy-

Example 1

Synthesis of [2-(2,6-dichloro-phenylamino)-phenyl]-acetic acid 4-(5-thioxo-5H-[1,2]dithiol-3-yl)-phenyl ester (Compound II)

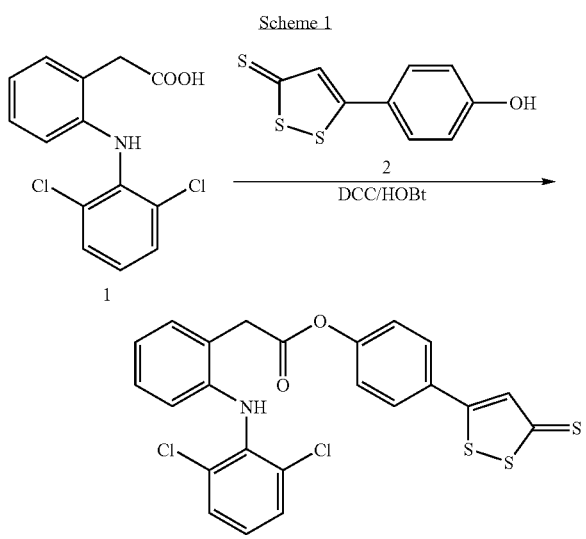

Synthesis of 5-p-hydroxyphenyl-1,2-dithiole-3-thione (2; ADT-OH)

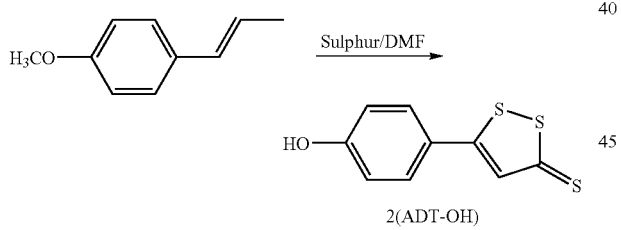

Anethole (31 g, 0.21 mol) and sulfur (44.8 g, 1.40 mol) were heated in N,N-dimethylformamide (250 ml) for 8 hrs; after removal of solvent, the residue was almost completely soluble in toluene. An attempt to extract the toluene liquors with 2N-aqueous sodium hydroxide, gave an orange solid precipitate (8.5 g; m.p. over 300° C.). This product was dissolved in boiling water and, after addition of hydrochloric acid, gave 2 as an orange precipitate (6.2 g, yield 13%) m.p. 188-189° C.

$^1$H NMR (DMSO-d$_6$) δ 6.86 (d, 2H), 7.68 (s, 1H), 7.75 (d, 2H), 10.51 (s, —OH); MS (ESI), m/z 225 (M'').

Synthesis of [2-(2,6-dichloro-phenylamino)-phenyl]-acetic acid 4-(5-thioxo-5H-[1,2]dithiol-3-yl)-phenyl ester (3)

To the solution of 1 (diclofenac, 890 mg, 3.0 mmol) in 50 mL of N,N-dimethylformamide, hydroxybenzotriazole (445 mg, 3.3 mmol) and DCC (680 mg, 3.3 mmol) were added with stirring at 0° C. for 1 h. To the reaction mixture 5-p-hydroxyphenyl-1,2-dithiole-3-thione (2; 678 mg, 3 mmol) was added and stirred for 1 h at 0° C. and 3 h at room temperature. After filtration, the filtrate was evaporated under reduced pressure and the oily residue thus obtained was dissolved in ethyl acetate; the organic layer was washed with brine, dried on anhydrous MgSO$_4$, filtered and the solvent evaporated. The crude product 3 was loaded on a silica gel open column and eluted with CH$_2$Cl$_2$/MeOH (9/1), from which [2-(2,6-dichloro-phenylamino)-phenyl]-acetic acid 4-(5-thioxo-5H-[1,2]dithiol-3-yl)-phenyl ester (3) was obtained (1.1 g, 74% yield).

$^1$H NMR (DMSO-d$_6$): δ 4.12 (s, 2H), 6.21 (d, 1H), 6.87 (t, 1H), 7.14 (t, 1H), 7.19 (d, 1H), 7.22 (t, 1H), 7.34 (d, 2H), 7.54 (d, 2H), 7.80 (s, 1H), 7.97 (d, 2H);

$^{13}$C NMR (DMSO-d$_6$): δ 37.4, 116.1, 121.0, 122.3, 123.5, 123.7, 127.0, 128.7, 129.3, 129.8, 132.0, 132.2, 136.4, 137.7, 143.8, 154.2, 170.3, 173.3, 213.2.

MS (EI), m/e 504 (M$^+$);

m.p.: 83-86° C.

Example 2

Synthesis of [2-(2,6-dichloro-phenylamino)-phenyl]-acetic acid 4-thiocarbamoyl-phenyl ester (Compound XVII)

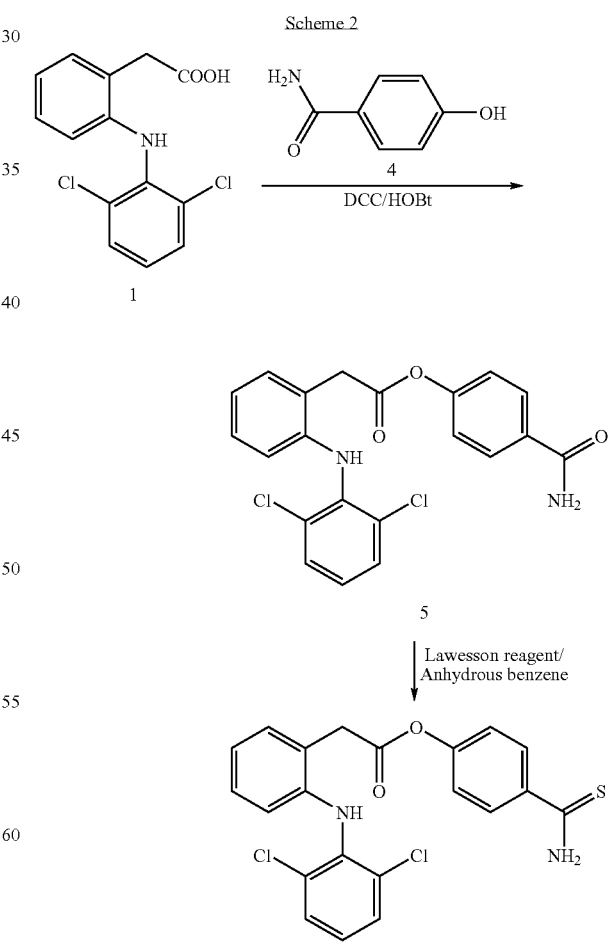

Synthesis of 4-carbamoylphenyl 2-[2-(2,6-dichlorophenylamino)-phenyl]acetate (5)

To the solution of 1 (diclofenac, 890 mg, 3.0 mmol) in 50 mL of N,N-dimethylformamide, hydroxybenzotriazole (445 mg, 3.3 mmol) and DCC (680 mg, 3.3 mmol) were added with stirring at 0° C. for 1 h. To the reaction mixture 4-hydroxybenzamide (4, 616 mg, 4.5 mmol) was added and stirred for 1 h at 0° C. and 3 hs at room temperature. After filtration, the filtrate was evaporated under reduced pressure and the oily residue thus obtained was dissolved in chloroform; the organic layer was washed with brine, dried on anhydrous MgSO$_4$, filtered and the solvent evaporated. The crude product 5 was loaded on a silica gel open column and eluted with CH$_2$Cl$_2$/MeOH (9/1), from which 4-carbamoylphenyl 2-(2-(2,6-dichlorophenylamino)phenyl)acetate (5) was obtained (212 mg, 17% yield).

Synthesis of [2-(2,6-dichloro-phenylamino)-phenyl]-acetic acid 4-thiocarbamoyl-phenyl ester (6)

4-Carbamoylphenyl 2-(2-(2,6-dichlorophenylamino)phenyl)acetate (5, 480 mg, 1.14 mmol) and Lawesson reagent (460 mg, 1.14 mmol) were dissolved in 20 ml of anhydrous benzene. The reaction was warmed to 50° C. and stirred for 6 h. The solvent was removed under reduced pressure; the crude residue was purified by silica gel column (dichloromethane/methyl alcohol 9.5/0.5) to furnish the pure compound 6 (446 mg, 91% yield).

$^1$H NMR (CDCl$_3$): δ 4.07 (s, 2H), 6.59 (d, 1H), 6.67 (s, 1H), 6.98 (t, 1H), 7.14 (t, 1H), 7.19 (d, 1H), 7.28 (t, 1H), 7.33 (d, 2H), 7.63 (s, 1H), 7.97 (d, 2H);

$^{13}$C NMR (DMSO-d$_6$): δ38.8, 118.8, 121.8, 122.6, 123.7, 124.4, 128.7, 129.1, 129.6, 131.2, 137.2, 137.8, 142.9, 153.5, 170.5, 193.2, 201.7

MS (EI), m/e 431 (M$^+$);

m.p.: 170-172° C.

Example 3

Synthesis of [2-(2-chloro-6-fluorophenylamino)-phenyl]-acetic acid 4-(5-thioxo-5H-[1,2]dithiol-3-yl)-phenyl ester (Compound III)

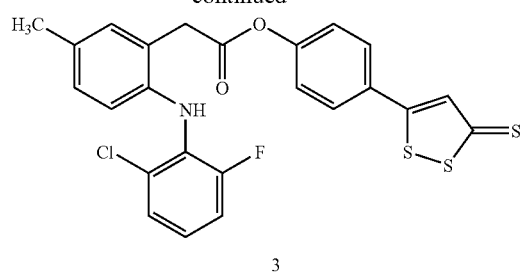

3

Synthesis of 4-(5-thioxo-5H-1,2-dithiol-3-yl)phenyl-2-(2-(2-chloro-6-fluorophenylamino)-5-methylphenyl)acetate (3)

To the solution of 1 (lumiracoxib, 600 mg, 2.03 mmol) in 40 mL of dimethylformamide, hydroxybenzotriazole (301 mg, 2.23 mmol) and DCC (459 mg, 2.23 mmol) were added with stirring at 0° C. for 1 h. To the reaction mixture 5-p-hydroxyphenyl-1,2-dithiole-3-thione (2; 504 mg, 2.23 mmol) was added and stirred for 1 h at 0° C. and 3 h at room temperature. After filtration, the filtrate was evaporated under reduced pressure to remove the solvent. The oily residue thus obtained was dissolved in ethyl acetate; the organic layer was washed with brine, dried on anhydrous MgSO$_4$, filtered and the solvent evaporated. The crude product 3 was loaded on a silica gel open column and eluted with CH$_2$Cl$_2$, from which 4-(5-thioxo-5H-1,2-dithiol-3-yl)phenyl-2-(2-(2-chloro-6-fluorophenylamino)-5-methylphenyl)acetate (3) was obtained (299 mg, 37% yield).

$^1$H NMR (DMSO): δ 2.32 (s, 3H), 4.02 (s, 2H), 6.41 (s, 1H), 6.71 (d, 1H), 6.93 (t, 1H), 6.95 (d, 2H), 7.14 (d, 1H), 7.19 (d, 2H), 7.39 (s, 1H), 7.66 (d, 2H);

$^{13}$C NMR (DMSO): δ20.8, 38.7, 115.2, 119.2, 122.5, 123.2, 124.0, 126.1, 127.2, 129.3, 130.3, 131.7, 132.2, 133.6, 136.4, 140.3, 153.7, 154.4, 156.8, 170.3, 171.6, 215.7

MS (EI), m/e 503 (M$^+$);

m.p.: ¶31-133° C.

Example 4

Synthesis of 4-thiocarbamoylphenyl 2-(2-(2-chloro-6-fluorophenylamino)-5-methylphenyl)acetate (Compound XVIII)

Scheme 1

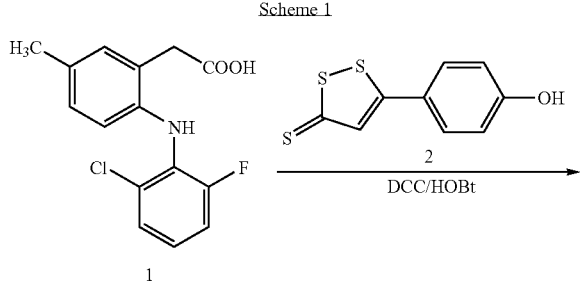

Scheme 2

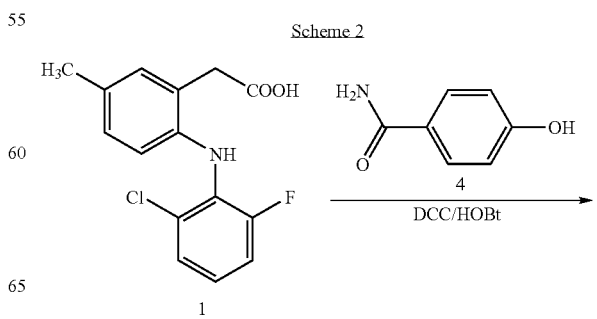

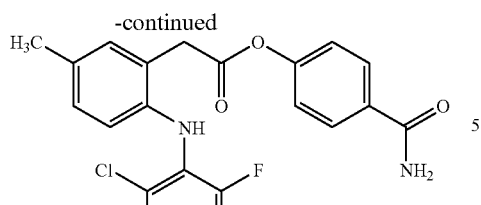

5

↓ Lawesson reagent/
Anhydrous benzene

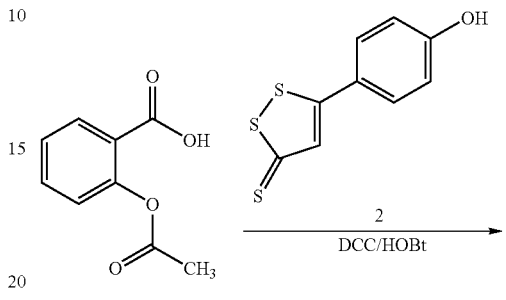

6

Synthesis of 4-carbamoylphenyl-2-(2-(2-chloro-6-fluorophenylamino)-5-methylphenyl)acetate (5)

To the solution of 1 (lumiracoxib, 223 mg, 0.75 mmol) in 15 mL of dimethylformamide, hydroxybenzotriazole (111 mg, 0.825 mmol) and DCC (170 mg, 0.825 mmol) were added with stirring at 0° C. for 1 h. To the reaction mixture 4-hydroxybenzamide (4, 154 mg, 1.125 mmol) was added and stirred for 1 h at 0° C. and 3 h at room temperature. After filtration, the filtrate was evaporated under reduced pressure to remove the solvent. The oily residue thus obtained was dissolved in chloroform; the organic layer was washed with brine, dried on anhydrous $MgSO_4$, filtered and the solvent evaporated. The crude product 5 was loaded on a silica gel open column and eluted with $CH_2Cl_2$/MeOH (9/1), from which 4-carbamoylphenyl-2-(2-(2-chloro-6-fluorophenylamino)-5-methylphenyl)acetate (5) was obtained (111 mg, 35% yield).

Synthesis of 4-thiocarbamoylphenyl-2-(2-(2-chloro-6-fluorophenylamino)-5-methylphenyl)acetate (6)

4-Carbamoylphenyl-2-(2-(2-chloro-6-fluorophenylamino)-5-methylphenyl)acetate, 5 (110 mg, 0.27 mmol) and Lawesson reagent (109 mg, 0.27 mmol) were dissolved in 15 ml of anhydrous benzene. The reaction was warmed to 60° C. and stirred for 3 h. The solvent was removed under reduced pressure; the crude residue was purified by silica gel column (dichloromethane/methyl alcohol 9.5:0.5) to furnish the pure compound 6 (59 mg, 51% yield).

$^1H$ NMR ($CDCl_3$): δ 2.32 (s, 3H), 4.01 (s, 2H), 6.46 (s, 1H), 6.70 (d, 1H), 6.92 (t, 1H), 7.01 (d, 2H), 7.11 (d, 2H), 7.19 (d, 1H), 7.62 (s, NH), 7.84 (d, 2H);

$^{13}C$ NMR (DMSO-$d_6$): 620.8, 30.7, 115.1, 119.2, 122.0, 122.3, 124.1, 124.9, 126.1, 128.2, 129.2, 132.3, 134.8, 138.6, 140.9, 153.7, 154.6, 156.2, 170.4, 201.7

MS (EI), m/e 429 ($M^+$);

m.p.: 120-122° C.

Example 5

Synthesis of 4-(5-thioxo-5H-1,2-dithiol-3-yl)phenyl 2-acetoxybenzoate (Compound I)

Scheme 1

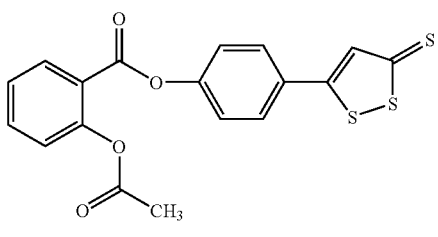

3

Synthesis of 4-(5-thioxo-5H-1,2-dithiol-3-yl)phenyl 2-acetoxybenzoate (3)

To the solution of 1 (acetylsalicylic acid, 416 mg, 2.31 mmol) in 40 mL of dimethylformamide, hydroxybenzotriazole (343 mg, 2.54 mmol) and DCC (523 mg, 2.54 mmol) were added with stirring at 0° C. for 1 h. To the reaction mixture 5-p-hydroxyphenyl-1,2-dithiole-3-thione (2; 574 mg, 2.54 mmol) was added and stirred for 1 h at 0° C. and 3 h at room temperature. After filtration, the filtrate was evaporated under reduced pressure to remove the solvent. The oily residue thus obtained was dissolved in ethyl acetate; the organic layer was washed with brine, dried on anhydrous $MgSO_4$, filtered and the solvent evaporated. The crude product was loaded on a silica gel open column and eluted with ethyl ether/petroleum ether (1/1), from which 4-(5-thioxo-5H-1,2-dithiol-3-yl)phenyl 2-acetoxybenzoate (3) was obtained (354 mg, 40% yield).

$^1H$ NMR (DMSO-$d_6$): δ 2.32 (s, 3H), 7.20 (d, 1H), 7.33 (d, 2H), 7.40 (s, 1H), 7.41 (t, 1H), 7.67 (t, 1H), 7.73 (d, 2H), 8.21 (d, 1H)

$^{13}C$ NMR (DMSO-$d_6$): δ21.3, 122.1, 123.4, 124.4, 126.6, 128.6, 129.7, 132.4, 135.4, 136.4, 151.6, 153.7, 162.6, 169.8, 171.9, 215.7

MS (EI), m/e 389 ($M^+$);

m.p.: 120-122° C.

Example 6

Synthesis of 2-Acetoxy-benzoic acid 4-thiocarbamoyl-pheny ester (Compound XVI)

Scheme 2

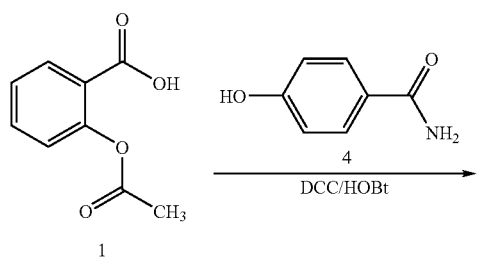

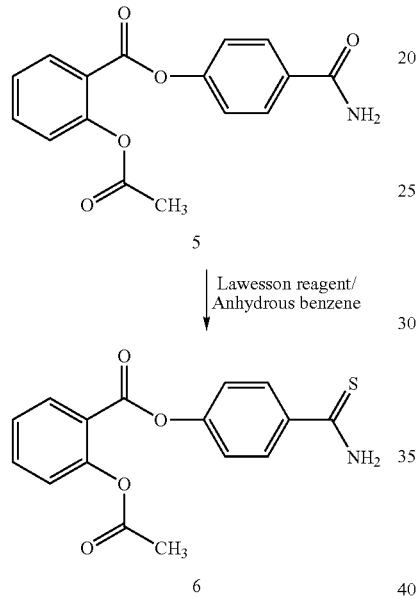

Synthesis of 4-carbamoylphenyl 2-acetoxybenzoate (5)

To the solution of 1 (acetylsalicylic acid, 500 mg, 2.77 mmol) in 15 mL of dimethylformamide, hydroxybenzotriazole (412 mg, 3.05 mmol) and DCC (628 mg, 3.05 mmol) were added with stirring at 0° C. for 1 h. To the reaction mixture 4-hydroxybenzamide (4, 418 mg, 3.05 mmol) was added and stirred for 1 h at 0° C. and 3 h at room temperature. After filtration, the filtrate was evaporated under reduced pressure to remove the solvent. The oily residue thus obtained was dissolved in chloroform; the organic layer was washed with brine, dried on anhydrous MgSO$_4$, filtered and the solvent evaporated. The crude product 5 was loaded on a silica gel open column and eluted with CH$_2$Cl$_2$/MeOH (9/1), from which 4-carbamoylphenyl 2-acetoxybenzoate (5) was obtained (410 mg, 47% yield).

Synthesis of 4-thiocarbamoylphenyl-2-(2-(2-chloro-6-fluorophenylamino)-5-methylphenyl) acetate (6)

4-Carbamoylphenyl 2-acetoxybenzoate, 5 (410 mg, 1.37 mmol) and Lawesson reagent (554 mg, 1.37 mmol) were dissolved in 35 ml of anhydrous benzene. The reaction was warmed to 60° C. and stirred for 3 h. The solvent was removed under reduced pressure; the crude residue was purified by silica gel column (dichloromethane/methyl alcohol 9.5:0.5) to furnish 470 mg of crude compound 6. The obtained compound was purified by preparative RP-HPLC carried out by two solvent systems: A: 100% acetonitrile in 0.1% TFA, B: 100% H$_2$O in 0.1% TFA (linear gradient from 10% A to 60% A over 35 min, UV detection at 254 nm, flow rate 30 mL/min) giving the pure compound 6 (324 mg, 71% yield).

$^1$H NMR (CDCl$_3$): δ 2.30 (s, 3H), 7.17 (d, 1H), 7.21 (d, 2H), 7.40 (t, 1H), 7.66 (t, 1H), 7.94 (d, 2H), 8.2 (d, 1H).
$^{13}$C NMR (DMSO-d$_6$): δ21.2, 121.9, 122.4, 124.3, 126.4, 128.7, 132.4, 135.1, 137.3, 151.5, 153.7, 162.7, 169.8, 201.8
MS (EI), m/e 316 (M$^+$);
m.p.: 154-156° C.

Example 7

Synthesis of [1-(4-Chloro-benzoyl)-5-methoxy-2-methyl-1-H-indol-3-yl]-acetic acid 4-(5-thioxo-5-H-[1,2]dithiol-3-yl)-phenyl ester (Compound IV)

Scheme 1

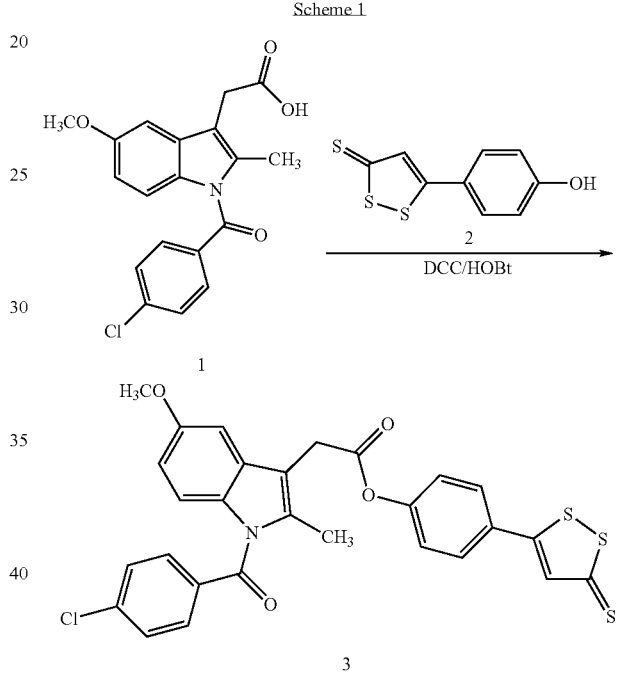

Synthesis of 4-[4-(5-thioxo-5H-1,2-dithiol-3-yl)]-phenyl-2-[1-(4-chlorobenzoyl)-5-methoxy-2-methyl-indol-3-yl]-acetate (3)

To the solution of 1 (indomethacin, 720 mg, 2.01 mmol) in 30 mL of dimethylformamide, hydroxybenzotriazole (301 mg, 2.21 mmol) and DCC (456 mg, 2.21 mmol) were added with stirring at 0° C. for 1 h. To the reaction mixture 5-p-hydroxyphenyl-1,2-dithiole-3-thione (2; 500 mg, 2.21 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with NaHCO$_3$ 5%, with citric acid 10% and than dried on anhydrous MgSO$_4$, filtered and the solvent evaporated. The crude product was loaded on a silica gel open column and eluted with dichloromethane/methyl alcohol (98/2), from which 4-[4-(5-thioxo-5H-1,2-dithiol-3-yl)]-phenyl-2-[1-(4-chlorobenzoyl)-5-methoxy-2-methyl-indol-3-yl]-acetate (3) was obtained (257 mg, 23% yield).

$^1$H NMR (CDCl$_3$): δ 2.47 (s, 3H), 3.84 (s, 3H, OCH$_3$), 3.93 (s, 2H), 6.70 (d, 1H), 6.88 (d, 1H), 7.04 (s, 1H), 7.21 (d, 2H), 7.37 (s, 1H) 7.48 (d, 2H), 7.65 (d, 2H), 7.67 (d, 2H)

$^{13}$C NMR (DMSO-d$_6$): δ 13.6, 30.8, 56.0, 101.5, 111.6, 111.9, 115.3, 122.9, 128.4, 129.4, 129.6, 130.6, 131.1, 131.4, 133.9, 136.3, 136.6, 139.7, 153.8, 156.4, 167.5, 168.9, 170.4, 215.7

MS (EI), m/e 567 (M$^+$);

m.p.: 90-92° C.

Example 8

Synthesis of [1-(4-Chloro-benzoyl)-5-methoxy-2-methyl-1-H-indol-3-yl]-acetic acid 4-thiocarbamoyl-phenyl ester (Compound XIX)

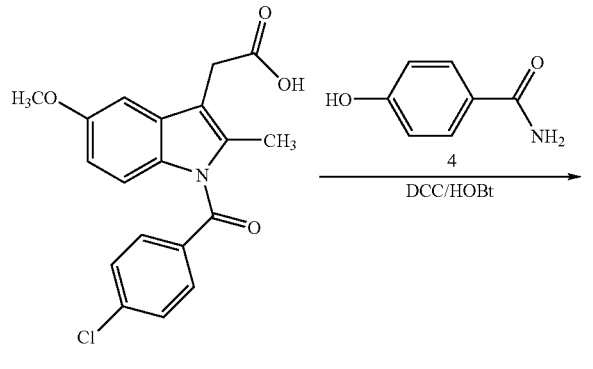

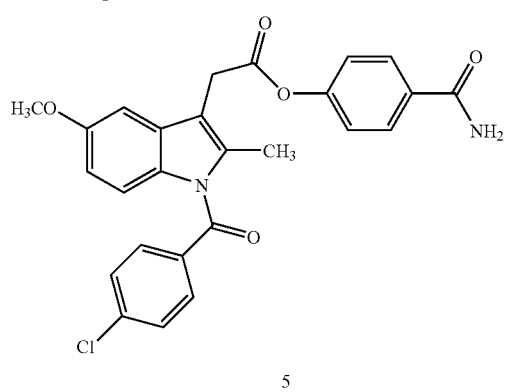

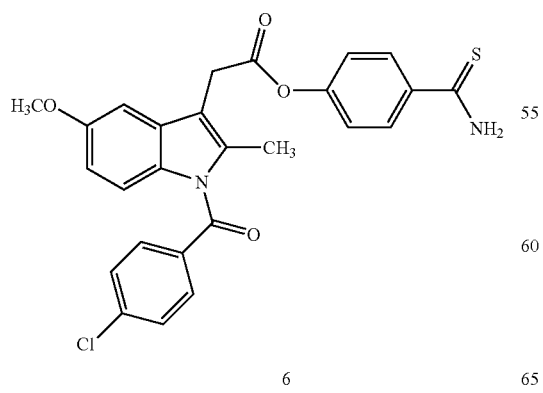

Synthesis of 4-carbamoylphenyl-2-[1-(4-chlorobenzoyl)-5-methoxy-2-methyl-indol-3-yl]acetate (5)

To the solution of 1 (indomethacin, 3 g, 8.38 mmol) in 60 mL of dimethylformamide, hydroxybenzotriazole (1.25 g, 9.22 mmol) and DCC (1.9 g, 9.22 mmol) were added with stirring at 0° C. for 1 h. To the reaction mixture 4-hydroxybenzamide (4, 1.72 g, 12.6 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with NaHCO$_3$ 5%, with citric acid 10% and than dried on anhydrous MgSO$_4$, filtered and the solvent evaporated. The crude product 5 was loaded on a silica gel open column and eluted with CH$_2$Cl$_2$/MeOH (9.5/0.5), from which 4-carbamoylphenyl-2-[1-(4-chlorobenzoyl)-5-methoxy-2-methyl-indol-3-yl]-acetate (5) was obtained (479 mg, 12% yield).

Synthesis of 4-thiocarbamoylphenyl-2-[1-(4-chlorobenzoyl)-5-methoxy-2-methyl-indol-3-yl]-acetate (6)

4-carbamoylphenyl-2-[1-(4-chlorobenzoyl)-5-methoxy-2-methyl-indol-3-yl]-acetate, 5 (340 mg, 0.71 mmol) and Lawesson reagent (287 mg, 0.71 mmol) were dissolved in 15 ml of anhydrous benzene. The reaction was warmed to 60° C. and stirred for 4 h. The solvent was removed under reduced pressure; the crude residue was purified by silica gel column (dichloromethane/methyl alcohol 9.5:0.5) to furnish 178 mg of crude compound 6. The obtained compound was purified by preparative RP-HPLC carried out by two solvent systems: A: 100% acetonitrile in 0.1% TFA, B: 100% H$_2$O in 0.1% TFA (linear gradient from 10% A to 80% A over 30 min, UV detection at 254 nm, flow rate 30 mL/min) giving the pure compound 6 (56 mg, 16% yield).

$^1$H NMR (CDCl$_3$): δ 2.45 (s, 3H), 3.83 (s, 3H, OCH$_3$), 3.91 (s, 2H), 6.70 (d, 1H), 6.88 (d, 1H), 7.04 (s, 1H), 7.11 (d, 2H), 7.47 (d, 2H), 7.67 (d, 2H), 7.88 (d, 2H).

$^{13}$C NMR (DMSO-d$_6$): δ13.6, 30.8, 56.0, 101.5, 111.9, 112.0, 115.3, 121.7, 128.6, 129.4, 130.8, 131.2, 131.4, 134.0, 136.8, 137.1, 139.7, 156.2, 157.9, 167.6, 169.8, 201.8

MS (EI), m/e 493 (M$^+$);

m.p.: 224-226° C.

Example 9

Synthesis of 2-(6-Methoxy-naphthale-2-yl)-propioic acid 4-(5-thioxo-5-H-[1,2]dithiol-3-yl)-phenyl ester (Compound V)

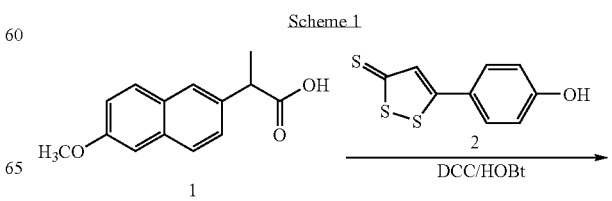

-continued

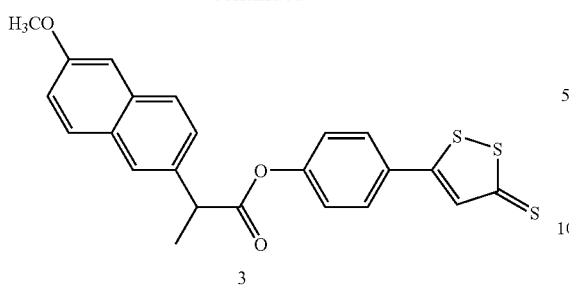

Synthesis of 4-(5-thioxo-5H-1,2-dithiol-3-yl)phenyl 2-(2-methoxynaphthalen-6-yl)propanoate (3)

To the solution of 1 (naproxen, 595 mg, 2.58 mmol) in 20 mL of dimethylformamide, hydroxybenzotriazole (388 mg, 2.87 mmol) and DCC (593 mg, 2.87 mmol) were added with stirring at 0° C. for 1 h. To the reaction mixture 5-p-hydroxyphenyl-1,2-dithiole-3-thione (2; 650 mg, 2.87 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with $NaHCO_3$ 5%, with citric acid 10% and than dried on anhydrous $MgSO_4$, filtered and the solvent evaporated. The crude product was loaded on a silica gel open column and eluted with dichloromethane, from which 4-(5-thioxo-5H-1,2-dithiol-3-yl)phenyl 2-(2-methoxynaphthalen-6-yl)propanoate (3) was obtained (406 mg, 36% yield).

$^1$H NMR (DMSO-$d_6$): δ 1.59 (d, 3H), 3.86 (s, 3H, $OCH_3$), 4.24 (dd, 1H), 7.18 (d, 1H), 7.22 (d, 2H), 7.31 (s, 1H), 7.50 (d, 1H), 7.77 (s, 1H) 7.85 (d, 1H), 7.86 (s, 1H), 7.87 (d, 1H), 7.91 (d, 2H)

$^{13}$C NMR (DMSO-$d_6$): δ 19.1, 45.2, 55.9, 106.5, 119.6, 123.5, 126.6, 126.9, 128.0, 129.2, 129.4, 129.5, 129.6, 129.9, 134.2, 135.6, 136.5, 154.2, 158.1, 173.2, 216.2

MS (EI), m/e 439 ($M^+$);

m.p.: 111-113° C.

Example 10

Synthesis of 2-(6-Methoxy-naphthalen-2-yl)-propionic acid 4-thiocarbamyl-phenyl ester (Compound XX)

Scheme 2

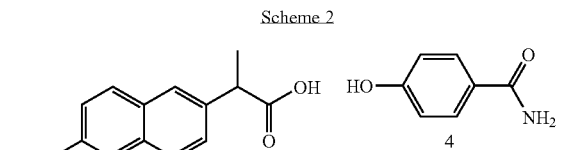

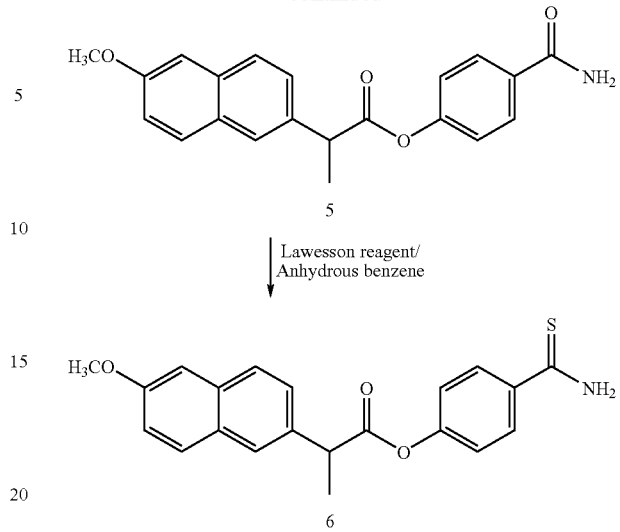

Synthesis of 4-carbamoylphenyl 2-(2-methoxynaphthalen-6-yl)propanoate (5)

To the solution of 1 (naproxen, 4 g, 17.4 mmol) in 80 mL of dimethylformamide, hydroxybenzotriazole (2.59 g, 19.14 mmol) and DCC (2.59 g, 19.14 mmol) were added with stirring at 0° C. for 1 h. To the reaction mixture 4-hydroxybenzamide (4, 3.58 g, 26.1 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with $NaHCO_3$ 5%, with citric acid 10% and than dried on anhydrous $MgSO_4$, filtered and the solvent evaporated. The crude product 5 was loaded on a silica gel open column and eluted with $CH_2Cl_2$/MeOH (9.5/0.5), from which 4-carbamoylphenyl 2-(2-methoxynaphthalen-6-yl)-propanoate (5) was obtained (1.91 g, 32% yield).

Synthesis of 4-thiocarbamoylphenyl 2-(2-methoxynaphthalen-6-yl)propanoate (6)

4-Carbamoylphenyl 2-(2-methoxynaphthalen-6-yl)-propanoate, 5 (1.80 g, 4.34 mmol) and Lawesson reagent (1.75 g, 4.34 mmol) were dissolved in 130 ml of anhydrous benzene. The reaction was warmed to 60° C. and stirred for 4 h. The solvent was removed under reduced pressure; the crude residue was purified by silica gel column (dichloromethane/methyl alcohol 9.75:0.25) to furnish 2.9 g of crude compound 6. The obtained compound was purified by a silica gel open column and eluted with $CH_2Cl_2$/MeOH (9.5/0.5)) giving the pure compound 6 (970 mg, 61% yield).

$^1$H NMR (DMSO-$d_6$): δ 1.59 (d, 3H), 3.86 (s, 3H, $OCH_3$), 4.24 (dd, 1H), 7.06 (d, 2H), 7.18 (d, 1H), 7.31 (s, 1H), 7.50 (d, 1H), 7.84 (s, 1H) 7.85 (d, 1H), 7.86 (s, 1H), 7.89 (d, 2H), 9.47 and 9.84 (s, 2H, $NH_2$). $^{13}$C NMR (DMSO-$d_6$): δ 19.1, 45.2, 55.9, 106.5, 119.6, 121.6, 126.6, 126.9, 128.0, 129.4, 129.9, 134.2, 135.6, 137.8, 153.4, 158.1, 173.3, 199.7.

MS (EI), m/e 366 ($M^+$);

m.p.: 196-198° C.

Example 11

Synthesis of 4-thiocarbamoylphenyl 2-(4-isobutylphenyl)propanoate (Compound XXIX)

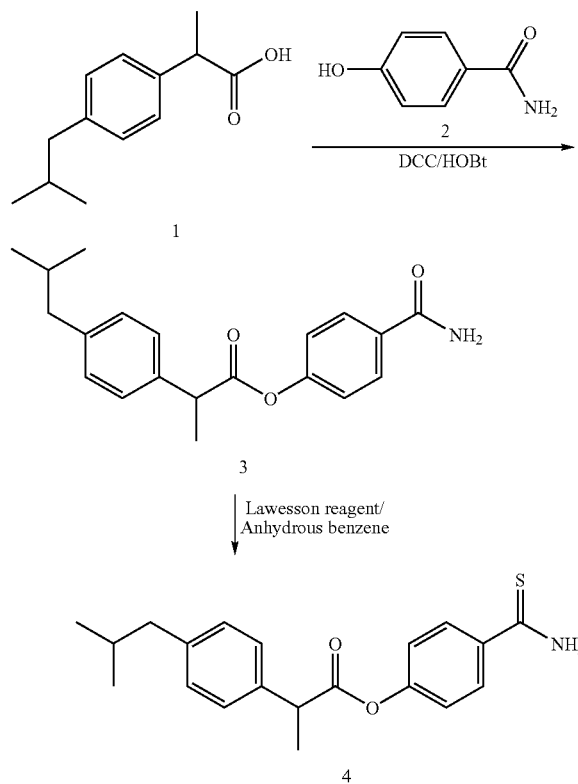

To the solution of 1 (ibuprofen, 3.87 g, 18.8 mmol) in 80 mL of dimethylformamide, hydroxybenzotriazole (2.8 g, 20.7 mmol) and DCC (4.27 g, 20.7 mmol) were added with stirring at 0° C. for 1 h. To the reaction mixture 4-hydroxybenzamide (2, 3.9 g, 28 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with NaHCO$_3$ 5%, with citric acid 10% and than dried on anhydrous MgSO$_4$, filtered and the solvent evaporated. The crude product 3 was loaded on a silica gel open column and eluted with CH$_2$Cl$_2$/MeOH (9.5/0.5), from which 4-carbamoylphenyl 2-(4-isobutylphenyl)propanoate (3) was obtained (2.48 g, 40% yield).

Synthesis of 4-thiocarbamoylphenyl 2-(4-isobutylphenyl)propanoate(4)

4-carbamoylphenyl 2-(4-isobutylphenyl)propanoate, 3 (2.48 g, 7.62 mmol) and Lawesson reagent (3.1 g, 7.62 mmol) were dissolved in 130 ml of anhydrous benzene. The reaction was warmed to 60° C. and stirred for 4 h. The solvent was removed under reduced pressure. The obtained compound was purified by a silica gel open column and eluted with CH$_2$Cl$_2$/MeOH (9.5/0.5) giving the pure compound 4 (1.45 g, 55% yield).

$^1$H NMR (DMSO-d$_6$): δ 0.84 (d, 6H), 1.48 (d, 3H), 1.79-1.82 (m, 1H), 2.42 (d, 2H), 4.05 (dd, 1H), 7.05 (d, 2H), 7.15 (d, 2H), 7.28 (d, 2H) 7.88 (d, 2H), 9.49 and 9.87 (s, 2H, NH$_2$).

$^{13}$C NMR (DMSO-d$_6$): δ 19.2, 22.9, 30.3, 44.9, 121.6, 127.9, 129.5, 130.0, 137.8, 138.0, 140.8, 153.3, 173.3, 199.6.
MS (EI), m/e 341 (M$^+$);
m.p: 121-123° C.

Example 12

Synthesis of 4-thiocarbamoylphenyl 2-(4-oxophenyl)-phenyl propanoate (Compound XXX)

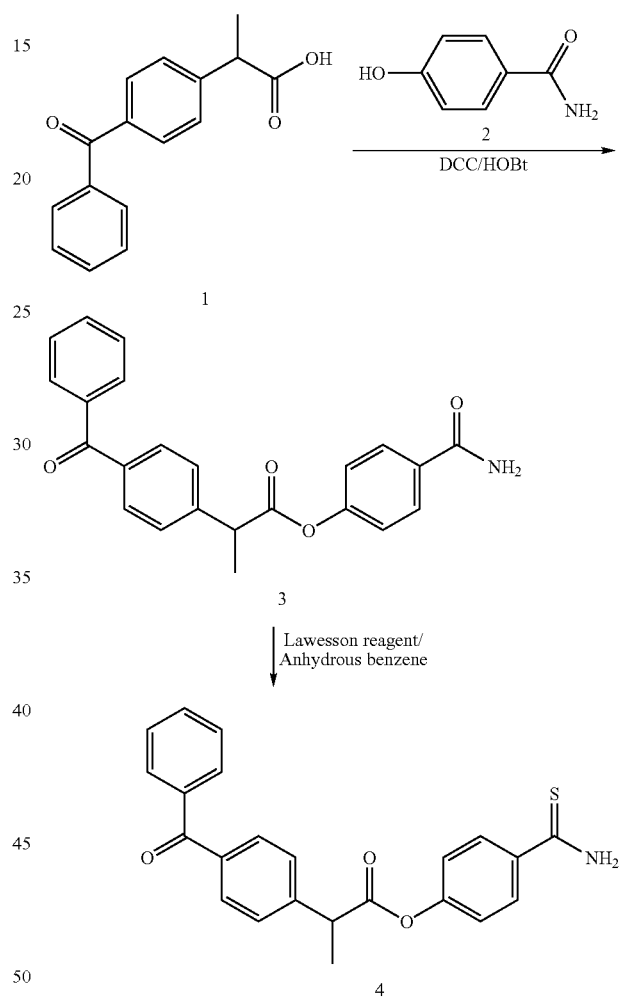

Synthesis of 4-carbamoylphenyl 2-(4-oxophenyl)-phenyl propanoate (3)

To the solution of 1 (ketoprofen, 3 g, 11.8 mmol) in 80 mL of dimethylformamide, hydroxybenzotriazole (1.76 g, 13 mmol) and DCC (2.68 g, 13 mmol) were added with stirring at 0° C. for 1 h. To the reaction mixture 4-hydroxybenzamide (2, 2.43 g, 17.7 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with NaHCO$_3$ 5%, with citric acid 10% and than dried on anhydrous MgSO$_4$, filtered and the solvent evaporated. The crude product 3 was loaded on a silica gel open column and eluted with CH$_2$Cl$_2$/MeOH (9.5/0.5), from which 4-carbamoylphenyl 2-(4-oxophenyl)-phenyl propanoate (3) was obtained (1.84 g, 42% yield).

Synthesis of 4-thiocarbamoylphenyl 2-(4-oxophenyl)-phenyl propanoate (4)

4-carbamoylphenyl 2-(4-oxophenyl)-phenyl propanoate (3) (1.84 g, 4.93 mmol) and Lawesson reagent (2 g, 4.93 mmol) were dissolved in 100 ml of anhydrous benzene. The reaction was warmed to 60° C. and stirred for 4 h. The solvent was removed under reduced pressure. The obtained compound was purified by a silica gel open column and eluted with CH$_2$Cl$_2$/MeOH (9.5/0.5) giving the pure compound 4 (0.45 g, 23% yield).

$^1$H NMR (DMSO-d$_6$): δ 1.53 (d, 3H), 4.25 (dd, 1H), 7.08 (d, 2H), 7.54-7.73 (m, 9H), 7.90 (d, 2H), 9.51 and 9.88 (s, 2H, NH$_2$).

$^{13}$C NMR (DMSO-d$_6$): δ 19.2, 44.9, 121.6, 129.3, 129.5, 129.8, 130.3, 132.6, 133.5, 137.6, 137.9, 138.1, 141.2, 153.3, 154.5, 156.1, 163.8, 172.9, 199.6.

MS (EI), m/e 390 (M$^+$);
m.p: 114-116° C.

Example 13

Synthesis of 4-thiocarbamoylphenyl 2-(3-fluoro, 4-phenyl)phenyl propanoate (Compound XXXI)

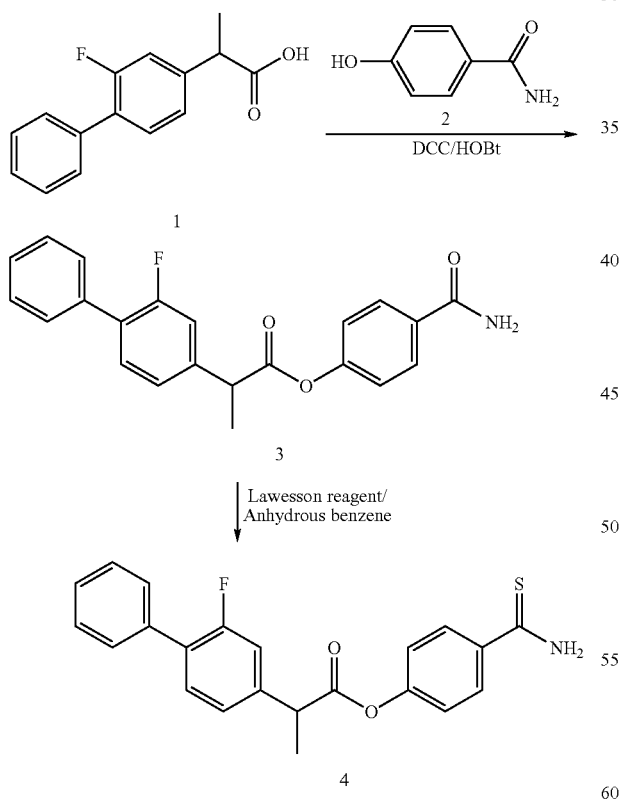

Synthesis of 4-carbamoylphenyl 2-(3-fluoro, 4-phenyl)phenyl propanoate (3)

To the solution of 1 (flurbiprofen, 2 g, 8.2 mmol) in 80 mL of dimethylformamide, hydroxybenzotriazole (1.22 g, 9.02 mmol) and DCC (1.86 g, 9.02 mmol) were added with stirring at 0° C. for 1 h. To the reaction mixture 4-hydroxybenzamide (2, 1.7 g, 12.2 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with NaHCO$_3$ 5%, with citric acid 10% and than dried on anhydrous MgSO$_4$, filtered and the solvent evaporated. The crude product 3 was loaded on a silica gel open column and eluted with CH$_2$Cl$_2$/MeOH (9.5/0.5), from which 4-carbamoylphenyl 2-(3-fluoro, 4-phenyl)phenyl propanoate (3) was obtained (1.09 g, 37% yield).

Synthesis of 4-thiocarbamoylphenyl 2-(3-fluoro, 4-phenyl)phenyl propanoate (4)

4-carbamoylphenyl 2-(3-fluoro, 4-phenyl)phenyl propanoate, 3 (1.09 g, 3 mmol) and Lawesson reagent (1.21 g, 3 mmol) were dissolved in 70 ml of anhydrous benzene. The reaction was warmed to 60° C. and stirred for 4 h. The solvent was removed under reduced pressure. The obtained compound was purified by a silica gel open column and eluted with CH$_2$Cl$_2$/MeOH (9.5/0.5) giving the pure compound 4 (0.35 g, 31% yield).

$^1$H NMR (DMSO-d$_6$): δ 1.55 (d, 3H), 4.21 (dd, 1H), 7.32-7.55 (m, 8H), 7.90 (d, 2H), 9.51 and 9.88 (s, 2H, NH$_2$).

$^{13}$C NMR (DMSO-d$_6$): δ 19.1, 44.7, 115.9, 116.2, 121.7, 124.8, 128.6, 129.3, 129.4, 129.5, 131.7, 135.8, 137.7, 142.6, 153.7, 158.3, 163.5, 173.1, 199.6.

MS (EI), m/e 380 (M$^+$);
m.p: 142-144° C.

Example 14

Synthesis of 4-(isothiocyano)-phenyl 2-(2-methoxynaphthalen-6-yl)propanoate (Compound XXV)

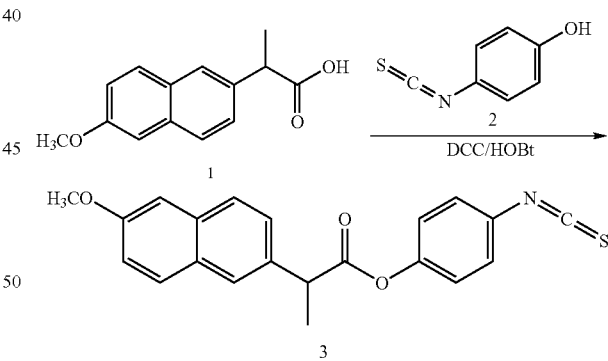

To the solution of 1 (naproxene, 691 mg, 3 mmol) in 20 mL of dimethylformamide, hydroxybenzotriazole (446 mg, 3.3 mmol) and DCC (619 mg, 3.3 mmol) were added with stirring at 0° C. for 1 h. To the reaction mixture 4-hydroxyphenylisothiocyanate (2; 500 mg, 3.3 mmol) was added and stirred for 1 h at 0° C. and 2 h at room temperature. After filtration, the filtrate was evaporated under reduced pressure to remove the solvent. The oily residue thus obtained was dissolved in ethyl acetate and the precipitate was removed. The solvent was evaporated and the crude product was loaded on a silica gel open column and eluted with dichloromethane, from which 4-(isothiocyano)-phenyl 2-(2-methoxynaphthalen-6-yl)propanoate (3) was obtained (230 mg, 21 yield).

¹H NMR (DMSO-d$_6$): δ 1.57 (d, 3H), 3.86 (s, 3H, OCH$_3$), 4.20 (dd, 1H), 7.10 (d, 2H), 7.15 (d, 1H), 7.29 (s, 1H), 7.43 (d, 2H), 7.48 (d, 1H), 7.78 (d, 1H) 7.80 (s, 1H), 7.83 (d, 1H).

¹³C NMR (DMSO-d$_6$): δ 19.1, 45.2, 55.9, 106.5, 119.6, 123.8, 126.6, 126.9, 128.0, 128.3, 129.2, 129.9, 134.2, 134.6, 135.7, 150.2, 158.1, 173.2, 215.1.

m. p. 66-68° C.; MS (EI), m/e 364 (M$^+$).

Example 15

Synthesis of 4-isothiocyanatophenyl 2-(2-(2,6-dichlorophenylamino)phenyl)acetate (Compound XXII)

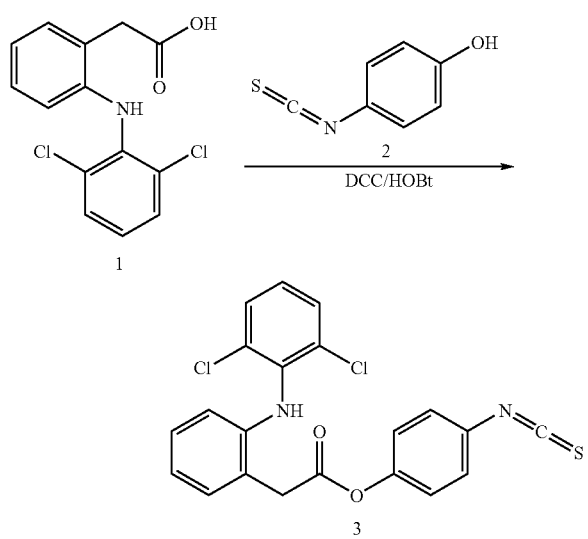

4-isothiocyanatophenyl 2-(2-(2,6-dichlorophenylamino)phenyl)acetate (3)

To the solution of 1 (diclofenac, 1717 mg, 5.8 mmol) in 60 mL of dimethylformamide, hydroxybenzotriazole (862 mg, 6.38 mmol) and DCC (1316 mg, 6.38 mmol) were added with stirring at 0° C. for 1 h. To the reaction mixture 4-hydroxyphenylisothiocyanate (2; 965 mg, 6.38 mmol) was added and stirred for 1 h at 0° C. and 2 h at room temperature. After filtration, the filtrate was evaporated under reduced pressure to remove the solvent. The oily residue thus obtained was dissolved in ethyl acetate and the precipitate was removed. The solvent was evaporated and the crude product was loaded on a silica gel open column and eluted with chloroform/n-hexane 9:1, from which 4-isothiocyanatophenyl 2-(2-(2,6-dichlorophenylamino)phenyl)acetate (3) was obtained (580 mg, 23% yield).

¹H NMR (DMSO-d$_6$): δ 4.09 (s, 2H), 6.19 (d, 1H), 6.83 (t, 1H), 7.05 (t, 1H), 7.14 (bs, 1H, NH), 7.21 (d, 2H), 7.25 (d, 2H), 7.47-7.54 (m, 3H).

¹³C NMR (DMSO-d$_6$): δ 37.4, 116.1, 121.0, 122.7, 124.0, 127.1, 127.8, 128.3, 128.7, 129.8, 132.0, 132.2, 137.7, 144.0, 150.3, 170.5, 215.1.

m. p. 132-134° C.; MS (EI), m/e 430 (M$^+$).

Example 16

Synthesis of 4-isothiocyanatophenyl 2-acetoxybenzoate (Compound XXI)

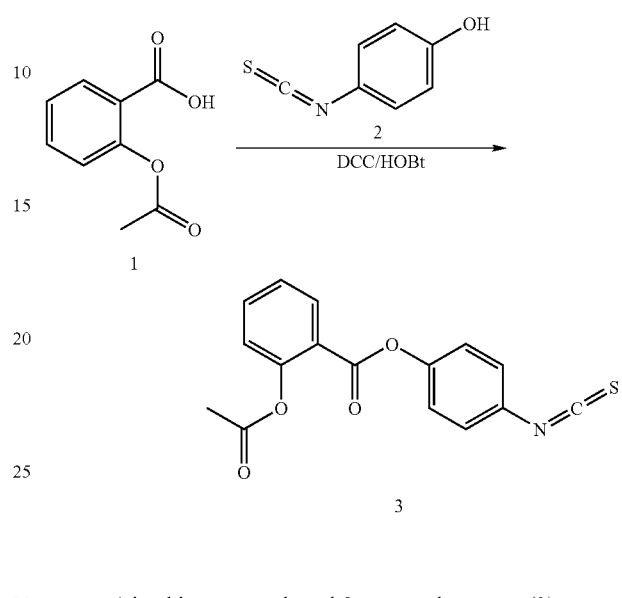

4-isothiocyanatophenyl 2-acetoxybenzoate (3)

To the solution of 1 (aspirin, 1200 mg, 6.67 mmol) in 60 mL of dimethylformamide, hydroxybenzotriazole (992 mg, 7.34 mmol) and DCC (1520 mg, 7.34 mmol) were added with stirring at 0° C. for 1 h. To the reaction mixture 4-hydroxyphenylisothiocyanate (2; 1109 mg, 7.34 mmol) was added and stirred for 1 h at 0° C. and 2 h at room temperature. After filtration, the filtrate was evaporated under reduced pressure to remove the solvent. The oily residue thus obtained was dissolved in ethyl acetate and the precipitate was removed. The solvent was evaporated and the crude product was loaded on a silica gel open column and eluted with chloroform/n-hexane 6:4, from which 4-isothiocyanatophenyl 2-acetoxybenzoate (3) was obtained (150 mg, 7% yield).

¹H NMR (CDCl$_3$): δ 2.31 (s, 3H), 7.17 (d, 1H), 7.19 (d, 2H), 7.29 (d, 2H), 7.38 (t, 1H), 7.66 (t, 1H, 8.20 (d, 1H).

¹³C NMR (CDCL$_3$): δ 21.3, 122.2, 123.3, 124.4, 126.6, 127.2, 129.4, 132.4, 135.2, 149.3, 151.5, 163.0, 170.0, 215.1.

m. p. 84-86° C.; MS (EI), m/e 272 (M$^+$).

Example 17

Gastrointestinal Safety of the Compounds of the Present Invention

Two diclofenac derivatives of the present invention, Compound II and Compound XVII, were evaluated for their gastrointestinal safety in rats. In particular, gastric damage, gastric PGE$_2$ synthesis, small intestine ulceration and hematocrit were measured.

Male Wistar rats weighing 175-200 g were fasted for 18 h prior to oral administration of 1% carboxymethylcellulose (vehicle; 0.2 mL) alone, or one of the following dissolved in this vehicle: diclofenac (20 mg/kg), Compound II (32 mg/kg), ADT-OH (12 mg/kg), diclofenac plus ADT-OH, Compound XVII (27.3 mg/kg), 4-hydroxythiobenzamide (TBZ) (7.3 mg/kg), the hydrogen sulfide releasing moiety on Compound XVII, or diclofenac plus TBZ. The doses of Compound II and Compound XVII are equimolar to a 20 mg/kg dose of diclofenac. Similarly, the doses of ADT-OH and TBZ are equimolar to the doses of Compound II and Compound XVII, respectively.

There were 5 rats in each group. Three hours after administration of the test compounds, the rats were euthanized and the extent of gastric hemorrhagic damage was blindly measured (in mm). A "gastric damage score" was produced by summing the lengths of all lesions in a stomach. With reference first to FIG. 1, no gastric damage was seen in the "vehicle", "Compound II" or "Compound XVII" groups. Compound II and Compound XVII elicited significantly less gastric damage than diclofenac. Moreover, a gastric-sparing effect was not observed if the NSAID moiety (diclofenac) and the $H_2S$-releasing moiety of Compound II and Compound XVII (ADT-OH and TBZ, respectively) were administered separately, but at the same time.

These observations were confirmed by subsequent, blind histological assessment. Samples (100-200) of gastric tissue were excised for measurement of prostaglandin $E_2$ ($PGE_2$) synthesis, as described in detail previously (Wallace et al., Cyclooxygenase 1 contributes to inflammatory responses in rats and mice: implications for gastrointestinal toxicity. *Gastroenterology* 1998; 115: 101-109, incorporated herein by reference). Briefly, the tissue samples were minced with scissors for 30 min, then placed in 1 mL of sodium phosphate buffer (pH 7.4) and placed in a shaking water bath (37° C.) for 20 min. Immediately thereafter, the samples were centrifuged for 1 min at 9,000 g and the supernatant was immediately frozen at −80° C. for subsequent measurement of $PGE_2$ concentration using a specific ELISA (Wallace et al., 1998).

Figure 2:
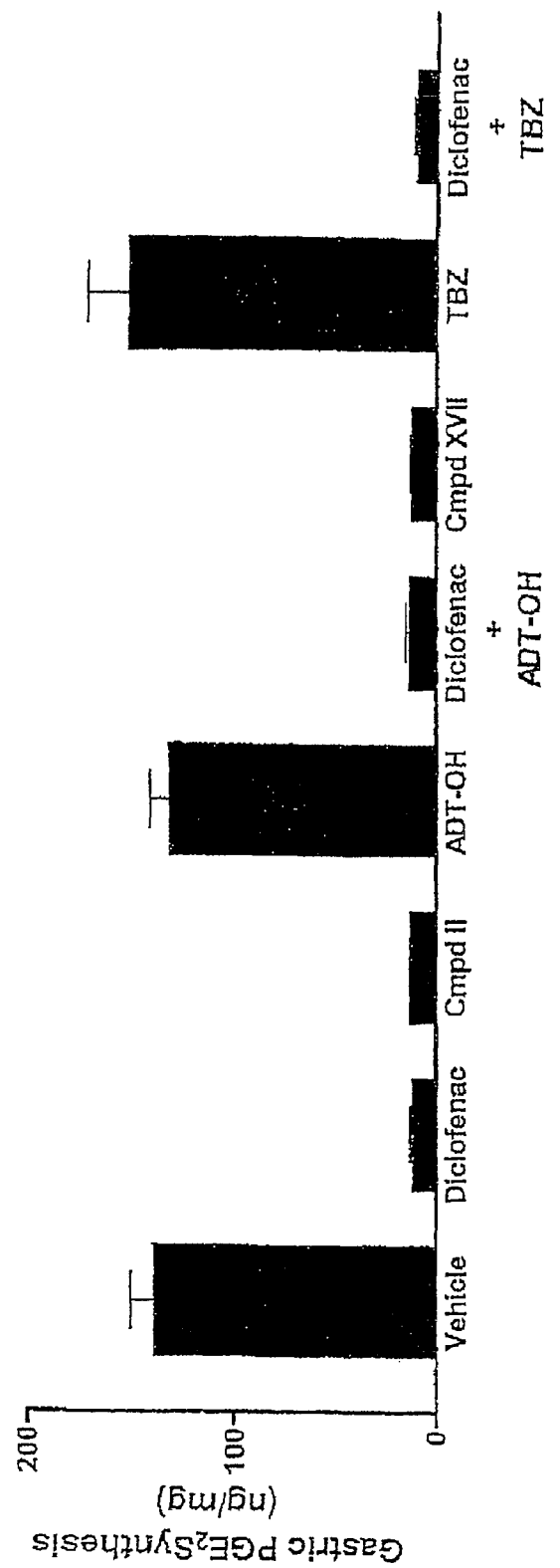
FIG. 2 illustrates the amount of gastric prostaglandin $E_2$ ($PGE_2$) produced in rats treated with vehicle, diclofenac, Compound II and Compound XVII.

With reference to FIG. 2, it can be seen that diclofenac (with or without concomitant administration of ADT-OH or TBZ), Compound II and Compound XVII all significantly reduced the amount of gastric $PGE_2$ synthesis, indicating inhibition of COX-1 and/or COX-2. ADT-OH and TBZ alone did not reduce gastric $PGE_2$ synthesis when compared to vehicle. Thus, the lack of gastric damage in rats treated with Compound II or Compound XVII as shown in FIG. 1 was not attributable to an alteration in the ability of these drugs to suppress gastric prostaglandin synthesis. Suppression of gastric $PGE_2$ synthesis was near-complete with these drugs, and with an equimolar dose of diclofenac.

Figure 3:
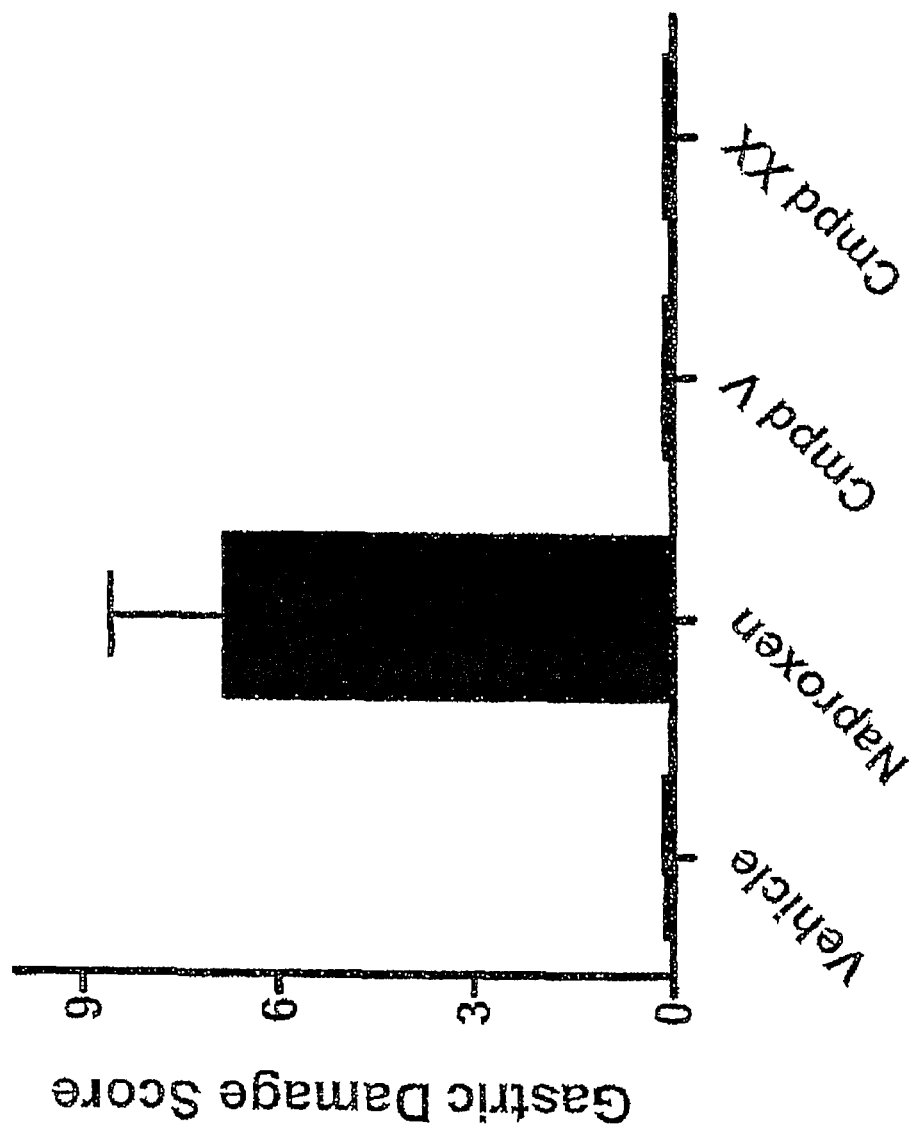
FIG. 3 illustrates the gastric damage score measured in rats treated with vehicle, naproxen, and two naproxen derivatives of the present invention, Compound V and Compound XX.

FIG. 3 shows that two naproxen derivatives of the present invention (Compounds V and XX) elicited significantly less damage than naproxen itself. These experiment were performed in exactly the same manner as those shown in FIG. 1. Naproxen, Compound V and Compound XX were each administered orally at a dose of 60 μmol/kg, and gastric damage was blindly evaluated 3 hours later. Gastric damage was not detectable in any of the rats treated with Compound V or Compound XX. Each group consisted of 5 rats. These observations were confirmed by subsequent, blind histological assessment.

Figure 4:
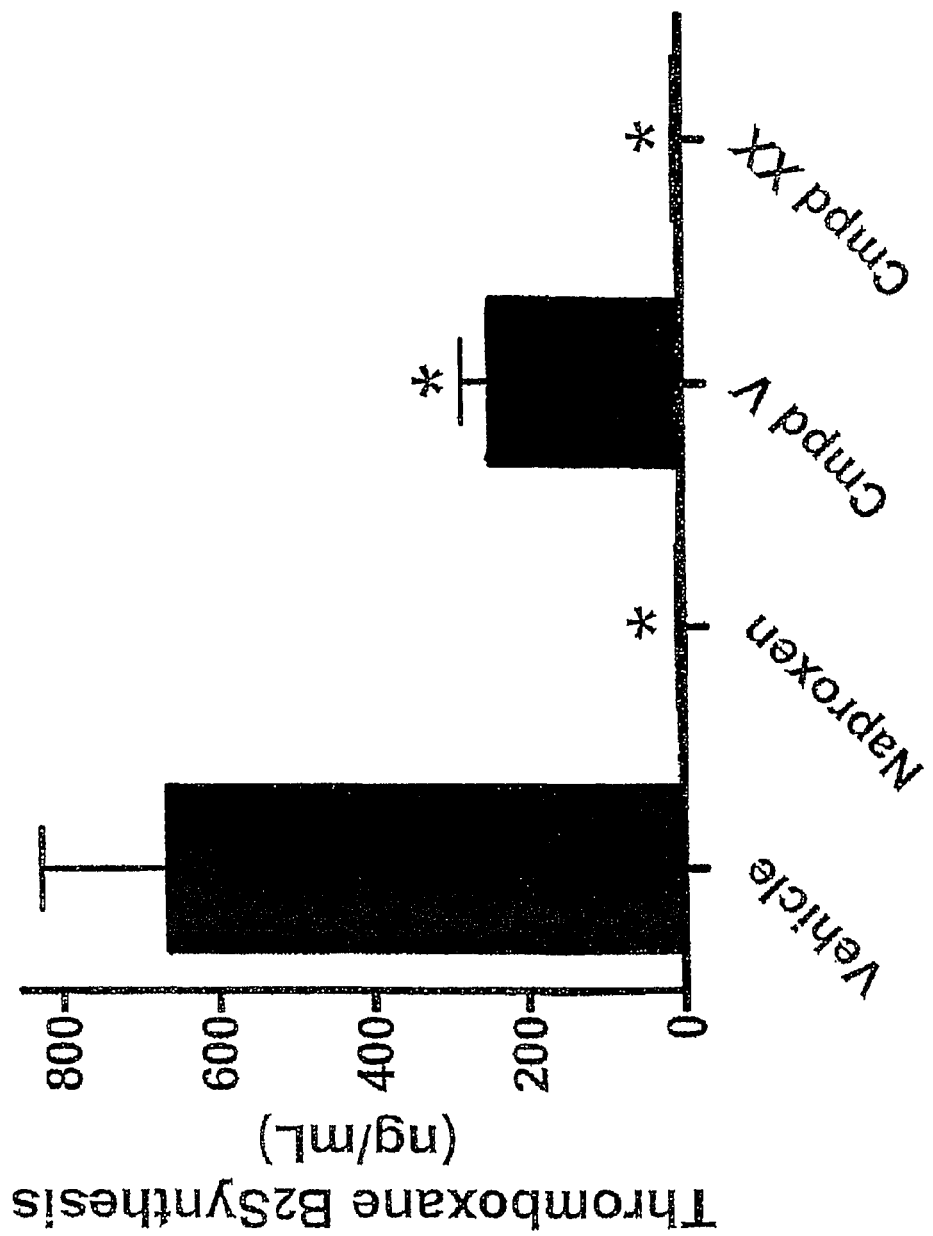
FIG. 4 illustrates the amount of thromboxane $B_2$ synthesis in blood of the rats of FIG. 3.

Inhibition of COX-1 was also measured using the same rats. Immediately after collecting the exudates from the pouch, 1 mL of blood was drawn from the inferior vena cava of each rat and was placed in a glass tube and allowed to clot for 45 min, as described previously (Wallace et al., *Gastroenterology* 1998). The samples were then centrifuged for 3 min at 9,000 g and the supernatant was frozen at −80° C. for subsequent measurement of thromboxane $B_2$ concentrations using a specific ELISA. As shown in FIG. 4, naproxen, Compound V and Compound XX all significantly ($*p<0.05$) inhibited COX-1 activity as compared to the vehicle-treated group. The extent of inhibition of COX-1 was somewhat less with Compound V than with naproxen or Compound XX.

NSAIDs can also cause significant small intestinal injury and the effects of diclofenac on induction of small intestinal injury after repeated administration was compared to Compound II. Groups of 5 male, Wistar rats were given diclofenac or Compound II at a dose of 50 μmol/kg at time 0 and again 12 and 24 hours later. Another group of rats received vehicle (1% carboxymethylcellulose).

Hematocrit, the portion of blood that consists of packed red blood cells, which is expressed as a percentage by volume, was measured in a sample of blood taken from a tail vein at the start of the experiment, and 24 h after the final dose of drugs. The rats were euthanized 24 h after the final dose of the drugs and the abdomen was opened. An investigator unaware of the treatments the rats had received measured the lengths of all hemorragic erosions/ulcers in the small intestine. A small intestinal damage score was calculated by summing the lengths of all of the lesions in each rat.

Figure 5:
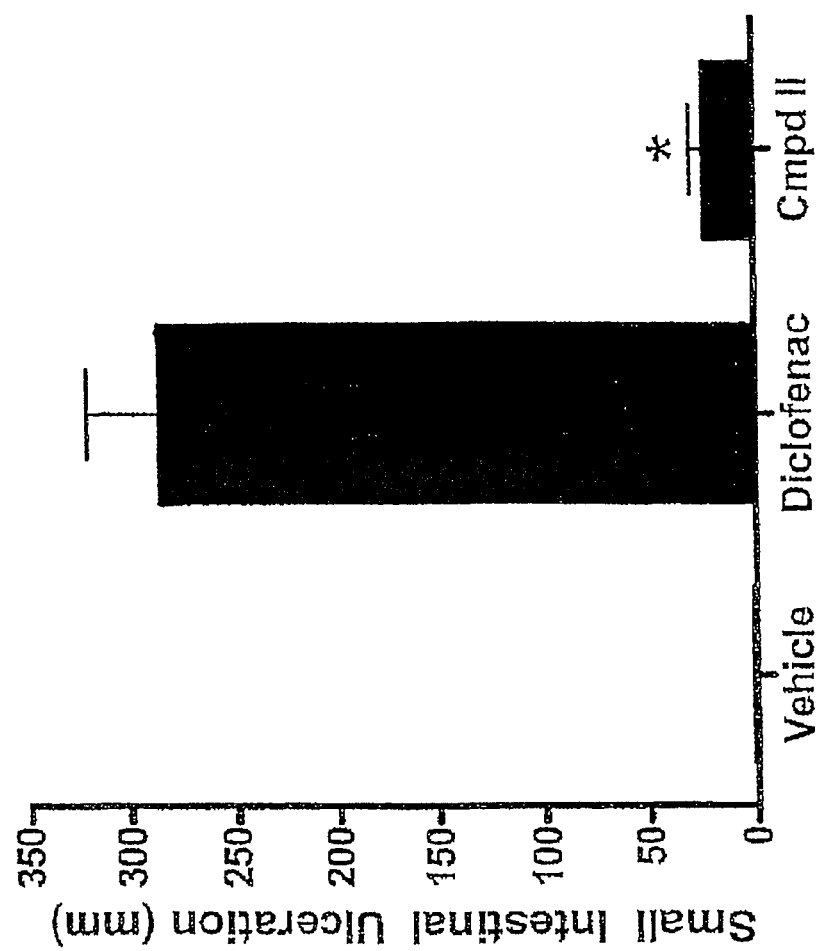
FIG. 5 illustrates the total length of small intestinal ulceration in rats treated with vehicle, diclofenac and Compound II.
Figure 6:
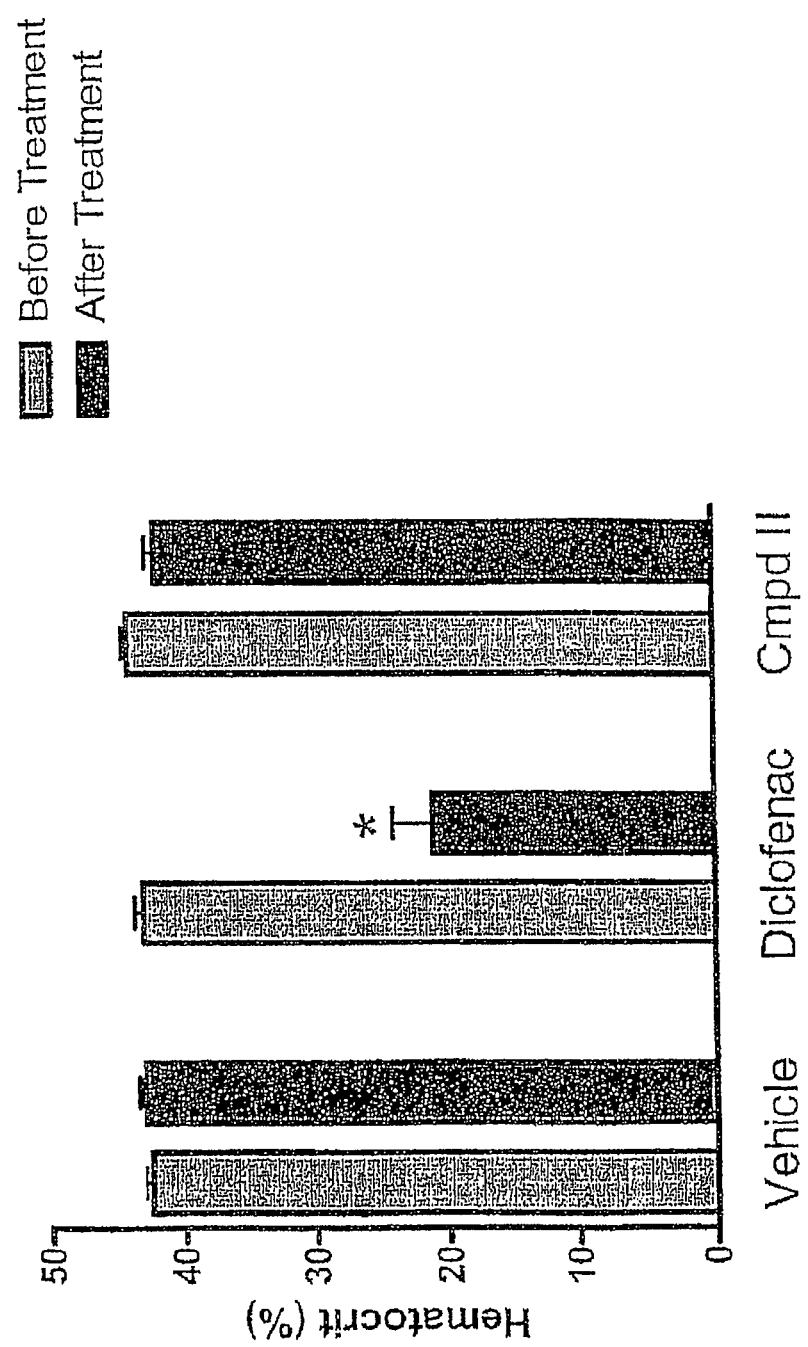
FIG. 6 illustrates the percent hematocrit in rats before and after being treated with vehicle, diclofenac and Compound II.

As shown in FIG. 5, administration of diclofenac three times over a 24-h period resulted in the development of extensive erosions and ulcers in the small intestine. On the other hand, the extent of damage observed in rats treated with Compound II was >90% less than that in the rats treated with diclofenac. Furthermore, as shown in FIG. 6, diclofenac treatment resulted in a profound reduction of hematocrit ($*p<0.05$), likely a result of small intestinal bleeding, whereas treatment with Compound II had no significant effect on hematocrit.

Example 18

Inhibition of Cyclooxygenase-2 (COX-2) and Cyclooxygenase-1 (COX-1)

Inhibition of COX-2 in vivo was determined using a modified version of a previously described model (Wallace et al., Limited anti-inflammatory efficacy of cyclo-oxygenase-2 inhibition in carrageenan-airpouch inflammation. *Br J Pharmacol* 1999; 126:1200-1204, incorporated herein by reference). Briefly, a subcutaneous "pouch" is created by repeated injections of air over several days. Once established, inflammation in the pouch can be induced by injection of 1 mL of 1% zymosan. This induces a large increase in prostaglandin $E_2$ ($PGE_2$) within the pouch, which has been shown to be derived almost exclusively from COX-2. Groups of 5 rats each were orally treated, 30 min before the carrageenan injection, with vehicle (1% carboxymethylcellulose), diclofenac (3 mg/kg), Compound II (4.8 mg/kg) or Compound XVII (4.1 mg/kg). Another group of 5 rats was treated with the vehicle, but received an injection of 0.9% sterile saline into the pouch rather than zymosan.

Figure 7:
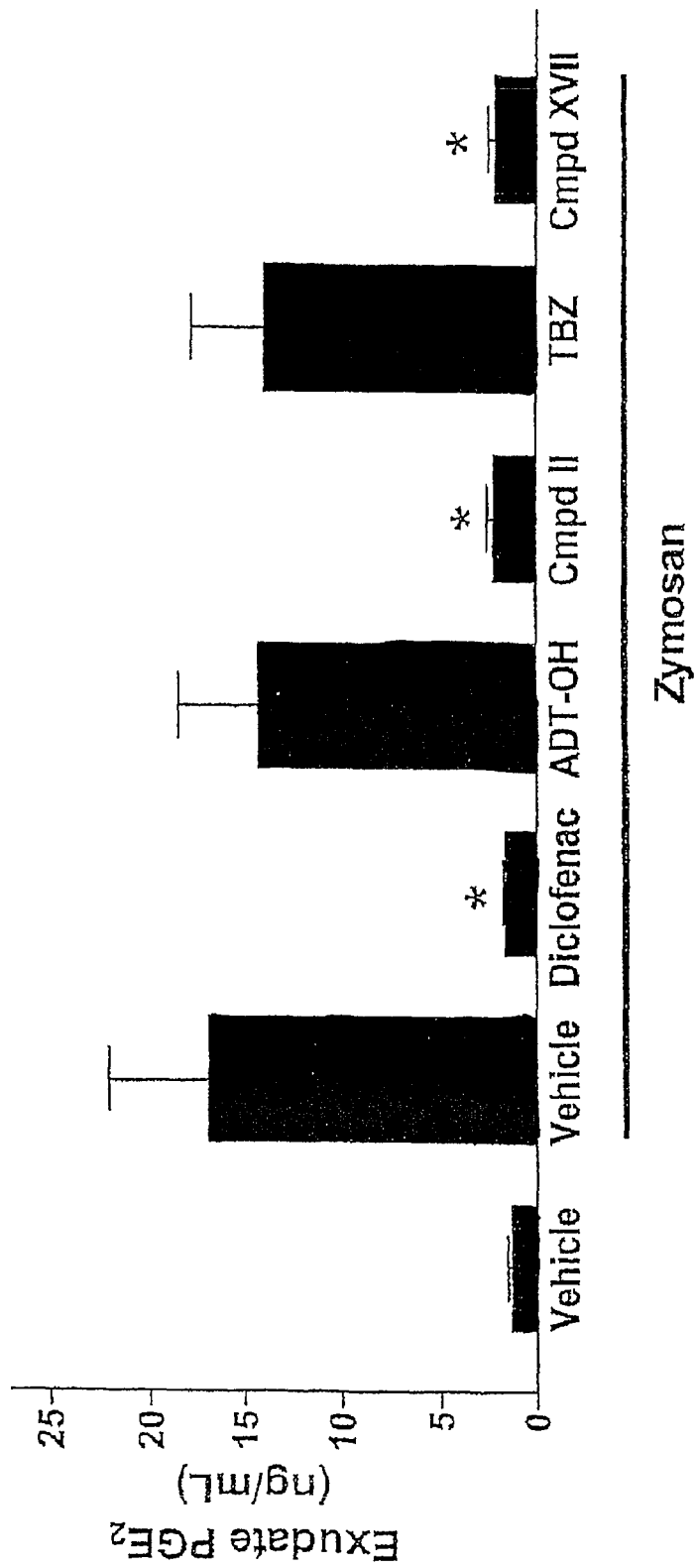
FIG. 7 illustrates the amount of exudate $PGE_2$ produced in the subcutaneous pouch of rats using the rat airpouch assay when treated with vehicle, diclofenac, Compound II and Compound XVII.

As can be seen in FIG. 7, pretreatment with diclofenac, Compound II or Compound XVII markedly reduced the concentrations of $PGE_2$ within the pouch that were produced in response to injection of zymosan. $*p<0.05$ versus the group treated with vehicle+zymosan. These results indicate that all three compounds significantly inhibited COX-2. In contrast, neither of the hydrogen sulfide releasing moieties (ADT-OH and TBZ) significantly affected COX-2 activity.

Figure 8:
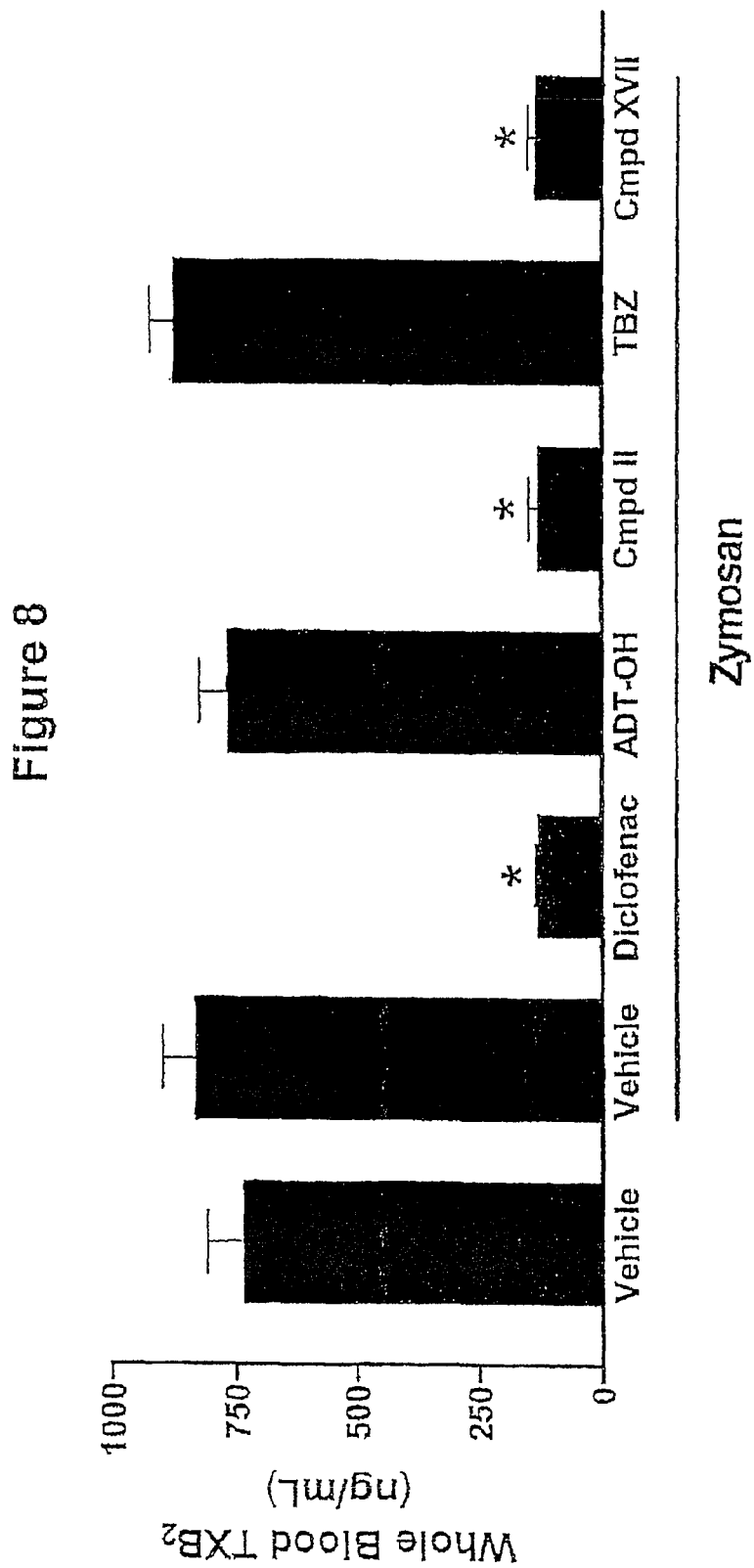
FIG. 8 illustrates the amount of whole blood thromboxane $B_2$ ($TXB_2$) in the rats of FIG. 7.

Inhibition of COX-1 was also measured using-the-same rats, using the same method as described for FIG. 4. As shown in FIG. 8, diclofenac, Compound II and Compound XVII each inhibited whole blood thromboxane synthesis, which occurs via COX-1, by greater than 80%. In contrast, neither of the hydrogen sulfide releasing moieties (ADT-OH and TBZ) significantly affected COX-1 activity.

Example 19

Effects of NSAID Derivatives on Gastric Damage, COX-1 and COX-2 Activity In Vivo The anti-inflammatory effects (COX-2 and COX-1 inhibition) and gastric safety of a number of compounds were compared using the assays described above. The results are summarized in Table 1. All of the parent NSAIDs caused significant gastric damage. However, the H$_2$S-releasing derivatives of the present invention showed improved gastric safety as compared to the parent drugs. It can also be seen from Table 1 that the TBZ derivatives either maintained or actually increased their ability to inhibit COX-1 and/or COX-2 when compared to the parent drug.

TABLE 1

Effects of NSAID Derivatives on Gastric Damage, COX-1 and COX-2 Activity In Vivo

| Compound | NSAID Moiety | H$_2$S Moiety | Dose (μmol/kg) | Gastric Damage | Inhibition of COX-1 | Inhibition of COX-2 |
|---|---|---|---|---|---|---|
| II | Diclofenac | ADT-OH | 30 | ↓ | ↓ | ↔ |
| XVII | Diclofenac | TBZ | 30 | ↓ | ↔ | ↔ |
| V | Naproxen | ADT-OH | 60 | ↓ | ↓ | ↔ |
| XX | Naproxen | TBZ | 60 | ↓ | ↔ | ↑ |
| IV | Indomethacin | ADT-OH | 30 | ↓ | ↔ | ↔ |
| XIX | Indomethacin | TBZ | 30 | ↓ | ↑ | ↔ |

Definitions
↑: statistically significant increase versus the parent drug ($p < 0.05$)
↓: statistically significant decrease versus the parent drug ($p < 0.05$)
↔: no significant change versus the parent drug
ADT-OH: 5-p-hydroxyphenyl-1,2-dithiole-3-thione
TBZ: 4-hydroxythiobenzamide Example 20

Effect of Compounds of the Present Invention on Inflammation

The anti-inflammatory effects of Compound II and Compound XVII with those of diclofenac were evaluated using the carrageenan hindpaw edema model as previously described in Wallace et al., *Gastroenterology* 1998. Male, Wistar rats weighing 175-200 g were given the test compounds orally 30 min prior to subplantar injection of 100 ul of 1% lambda carrageenan. Paw volume measured using an Ugo Basile hydroplethysmometer prior to carrageenan injection and at 1-h intervals thereafter for 5 h. Each group, which consisted of 5 rats, were treated with diclofenac at doses of 1, 3 or 10 mg/kg, or with Compound II or Compound XVII at doses equimolar to diclofenac at 3 mg/kg.

Figure 9:
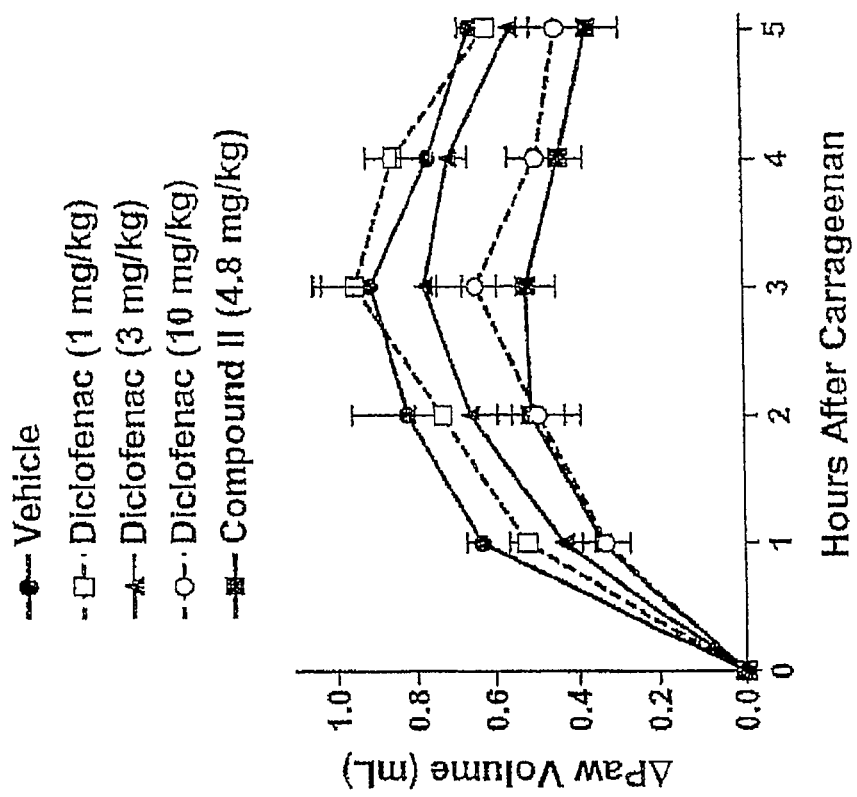
FIG. 9 illustrates the inhibition of paw volume increase in rats treated with vehicle, diclofenac and Compound II.
Figure 10:
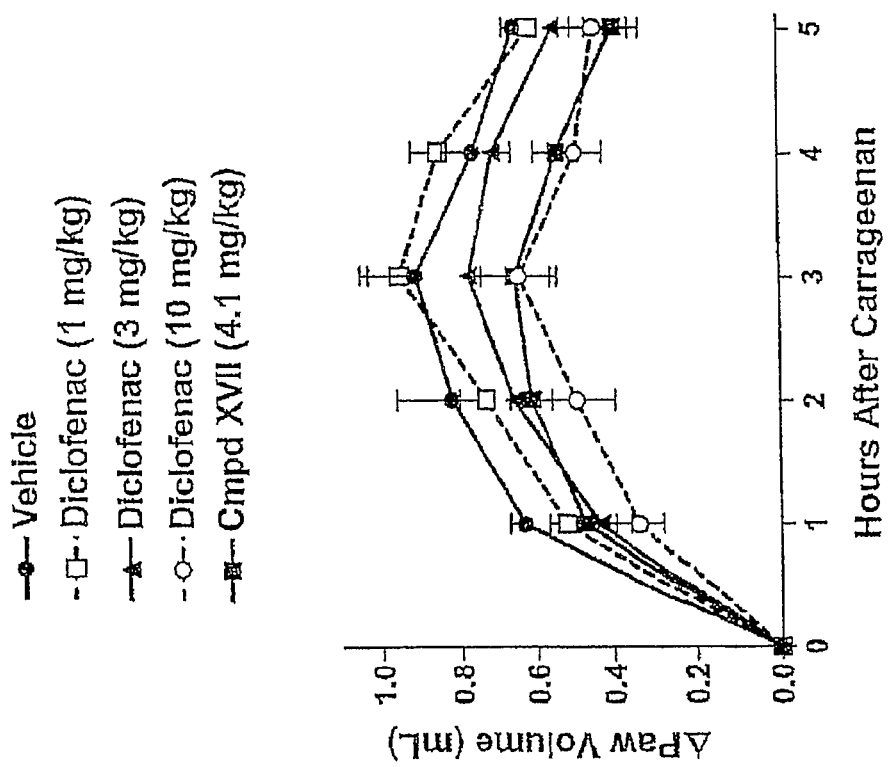
FIG. 10 illustrates the inhibition of paw volume increase in rats treated with vehicle, diclofenac and Compound XVII.

As shown in FIG. 9, diclofenac dose-dependently reduced paw edema induced by subplantar injection of carrageenan. Compound II, given at a dose equimolar to diclofenac at 3 mg/kg, reduced paw edema to a greater extent. Indeed, the effect of Compound II on paw edema was comparable to the effect of diclofenac at a dose of 10 mg/kg. Similarly, as shown in FIG. 10, Compound XVII, which was also given at a dose equimolar to diclofenac at 3 mg/kg, reduced paw edema to a greater extent, comparable to the effect of diclofenac at a dose of 10 mg/kg.

Because both Compound II and Compound XVII suppress prostaglandin synthesis to the same extent as diclofenac, the enhanced activity of the new compounds of the invention in the paw edema model is most likely related to another attribute of these compounds. It has previously been demonstrated that hydrogen sulfide donors can significantly reduce carrageenan-induced paw edema in the rat (Zanardo et al., Hydrogen sulphide is an endogenous modulator of leukocyte-mediated inflammation. *FASEB J* 2006; 20: 2118-2120, incorporated herein by reference), so, without being bound to theory, it is likely that H$_2$S release from Compound II and Compound XVII accounts for the enhanced anti-inflammatory effects in comparison to diclofenac.

Figure 11:
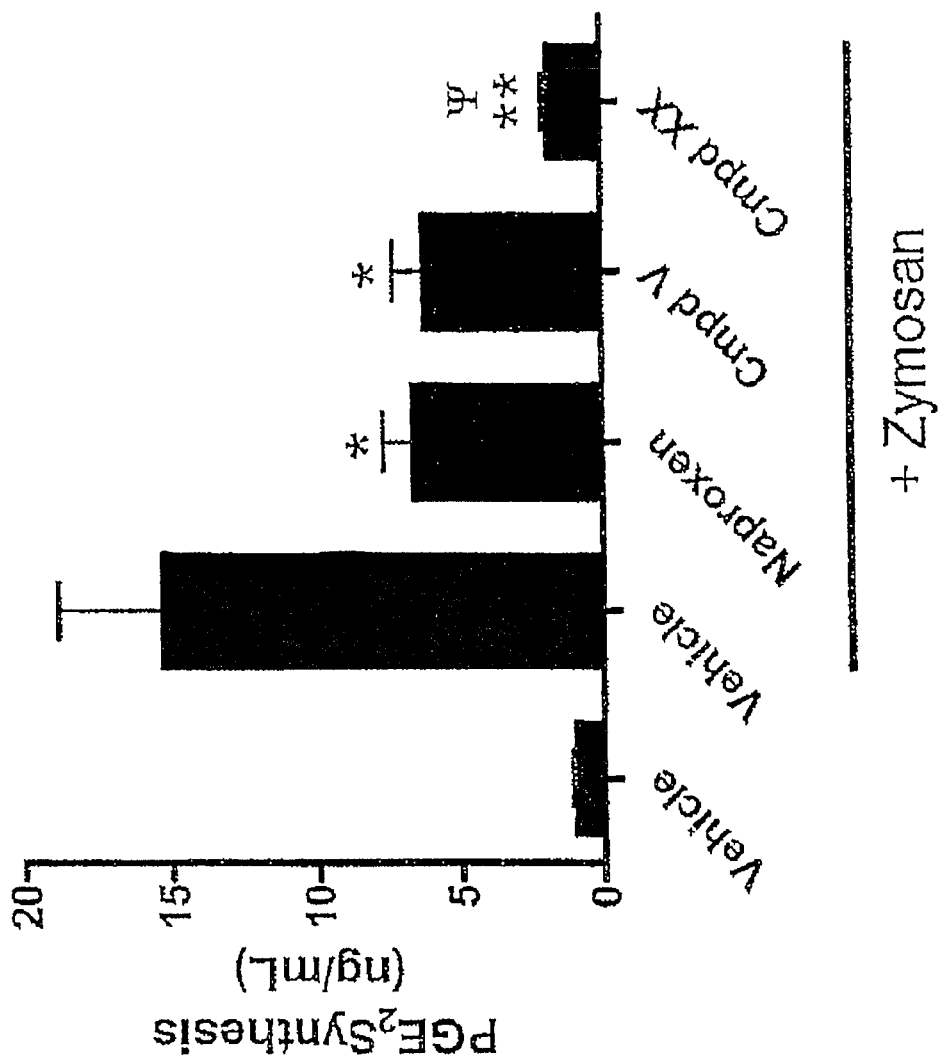
FIG. 11 illustrates the amount of exudate $PGE_2$ produced in the subcutaneous pouch of rats using the rat pouch assay when treated with vehicle, naproxen, Compound V and Compound XX.

Without being bound to theory, it is also possible that some of the additional activity of the compounds of this invention in models of inflammation may be attributable to enhanced inhibition of COX-2 activity. The effects of vehicle, naproxen, Compound V and Compound XX were compared in the rat airpouch model (as described for FIG. 7). Each group consisted of 5 rats. Naproxen, Compound V and Compound XX were each administered at a dose of 60 μmol/kg. As shown in FIG. 11, all three drugs significantly suppressed COX-2 activity as compared to the group treated with vehicle (*$p<0.05$, **$p<0.01$). However, Compound XX elicited a significantly greater reduction of COX-2 activity than was seen with naproxen or Compound V ($^\psi p<0.05$).

Figure 12:
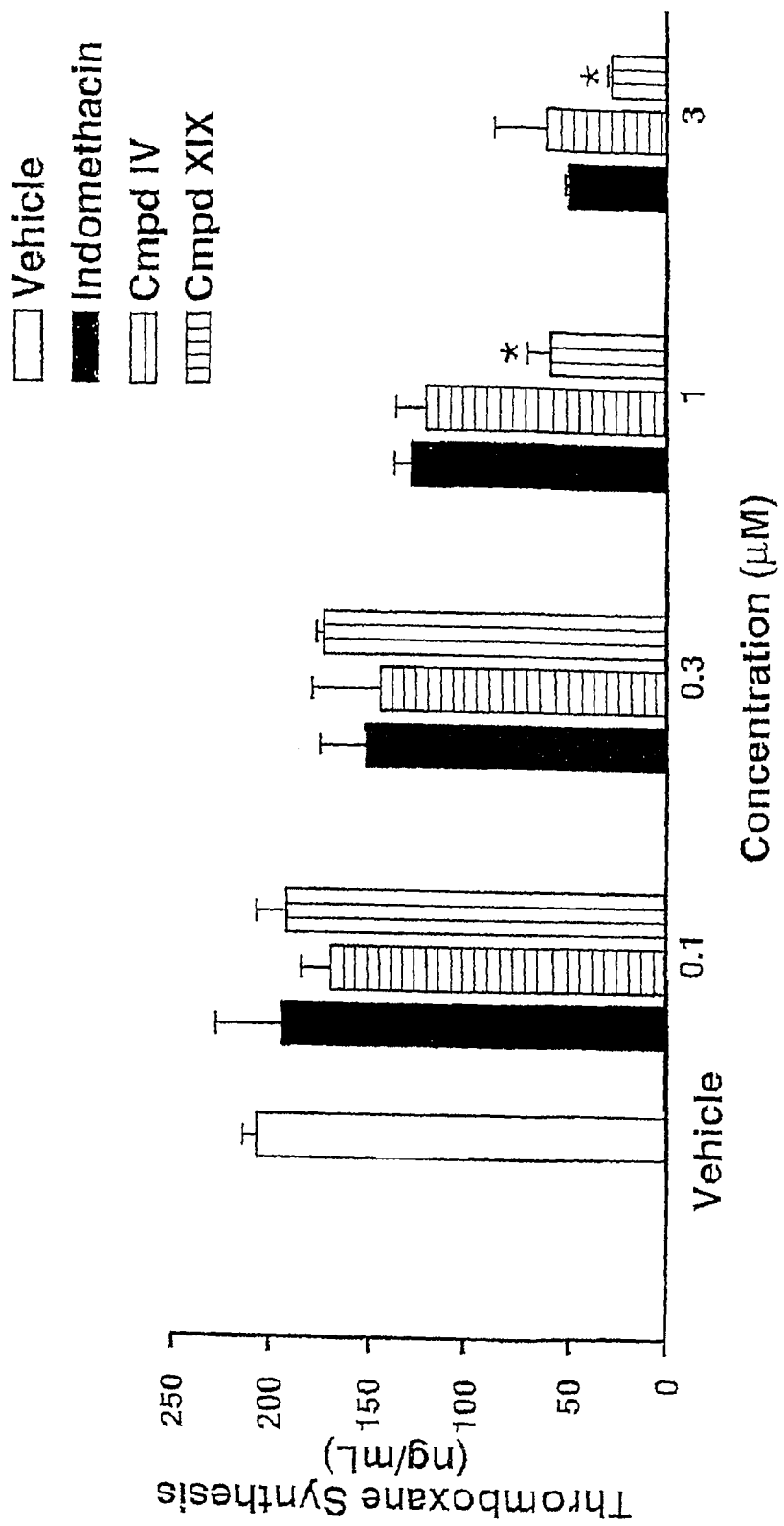
FIG. 12 illustrates thromboxane synthesis (ng/mL) by human blood (in vitro) as a function of concentration of indomethacin, Compound IV and Compound XIX.

Without being bound to theory, it is also possible that some of the additional activity of the compounds of this invention in models of inflammation may be attributable to enhanced inhibition of COX-1 activity. The effects of vehicle, indomethacin, and two compounds of this invention, Compound IV and Compound XIX, were compared for their effects on human whole blood thromboxane B$_2$ synthesis in vitro. Aliquots (0.5 mL) of blood from healthy human volunteers were added to glass tubes containing 10 uL of methanol alone, or one of the test drugs prepared such that the final concentration would be 0.1, 0.3, 1 or 3 μM. The tubes were placed in water bath (37° C.) with gentle shaking for 45 min, after which they were centrifuged (1,000×g) for 10 minutes. The concentration of thromboxane B$_2$ in each sample was then determined using a specific ELISA, as in the studies shown in FIG. 4. As shown in FIG. 12, all three drugs produced a concentration-dependent inhibition of COX-1 activity as compared to the vehicle-treated group. However, at concentrations of 1 and 3 μM, Compound XIX, produced a significantly greater (*$p<0.05$) inhibition of COX-1 activity than that produced by indomethacin.

Example 21

Leukocyte Adherence to the Vascular Endothelium of Compounds of the Present Invention Leukocyte adherence to the vascular endothelium is an early event in inflammatory reactions and contributes to thrombus formation. Hydrogen sulfide donors have been shown to reduce leukocyte adherence induced by aspirin or by the pro-inflammatory tripeptide, fMLP (Zanardo et al., *FASEB J* 2006; 20: 2118-2120). The effects of several derivatives of NSAIDs of the present invention on leukocyte adherence were evaluated using intravital microscopy in the rat, as described in detail by Zanardo et al. *FASEB J* 2006; 20: 2118-2120.

Briefly, post-capillary mesenteric venules in anestheitized rats are examined under a light microscope. After a basal recording period of 5 min, one of the test compounds listed in Table 2 below was administered intragastrically at a dose of 30 µmol/kg, with the exception of naproxen and the naproxen derivatives (Compounds V and XX), which were administered at a dose of 60 µmol/kg. All test compounds were prepared in a vehicle of 1% carboxymethylcellulose. Changes in leukocyte adherence within the venule were recorded with a video camera attached to the microscope, and quantification of the numbers of adherent leukocytes was performed in a blind manner through evaluation of the videotaped images. Each group consisted of 5 male, Wistar rats weighing 150-175 g. A leukocyte was considered "adherent" if it remained stationary for 30 seconds or more (results below are expressed as the mean±SEM). At the end of the experiment the stomach was opened and examined for the presence of gastric damage, under a dissecting microscope.

TABLE 2

Leukocyte Adherence to the Vascular Endothelium

| Compound Tested | Number of Adherent Leukocytes (per 100 µm vessel length) | Percent Incidence of Gastric Damage |
|---|---|---|
| Vehicle (1%) | 2.0 ± 0.2 | 0 |
| Aspirin | 7.1 ± 0.4* | 80 |
| Compound I | 2.5 ± 0.3 | 20 |
| Compound XVI | 2.3 ± 0.3 | 0 |
| Diclofenac | 8.6 ± 0.6* | 100 |
| Compound II | 3.0 ± 0.5 | 0 |
| Compound XVII | 2.8 ± 0.5 | 20 |
| Lumiracoxib | 9.3 ± 1.0* | 0 |
| Compound III | 1.7 ± 0.3 | 0 |
| Compound XVIII | 2.3 ± 0.4 | 0 |
| Indomethacin | 14.4 ± 0.7* | 100 |
| Compound IV | 3.6 ± 0.7 | 20 |
| Compound XIX | 3.0 ± 0.4 | 0 |
| Naproxen | 10.2 ± 0.4* | 100 |
| Compound V | 3.5 ± 0.7 | 0 |
| Compound XX | 2.3 ± 0.5 | 0 |

*p < 0.05 versus the vehicle-treated group (ANOVA and Dunnett's Multiple Comparison Test).

It can be seen from Table 2 that derivatives of aspirin of the present invention, in particular, Compound XVI and Compound I, both significantly reduced the number of adherent leukocytes per 100 µm vessel length when compared to aspirin alone. In addition, both Compound XVI and Compound I significantly reduced the percent incidence of gastric damage when compared to aspirin alone. Similarly, Table 2 further shows that derivatives of diclofenac of the present invention, in particular, Compound II and Compound XVII, significantly reduced the number of adherent leukocytes per 100 µm vessel length and significantly reduced the percent incidence of gastric damage when compared to diclofenac alone. Likewise, Table 2 further shows that derivatives of naproxen of the present invention, in particular, Compound V and Compound XX, significantly reduced the number of adherent leukocytes per 100 µm vessel length and significantly reduced the percent incidence of gastric damage when compared to naproxen alone.

Interestingly, derivatives of lumiracoxib, a COX-2 selective inhibitor having reduced gastric side effect, in particular, Compound III and Compound XVIII, still showed no incidences of gastric damage but both derivatives significantly reduced the number of adherent leukocytes per 100 µm vessel length when compared to lumiracoxib alone. Thus, covalently linking a hydrogen sulfide releasing moiety to COX-2 selective NSAIDs might reduce the cardiovascular side effects of these COX-2 inhibitors as well.

Thus, the NSAID derivatives of the present invention may result in reduced cardiovascular side effects of the NSAID by reducing leukocyte adherence.

Example 22

Effects of Compounds of the Present Invention on Gastric Ulcer Healing

Figure 13:
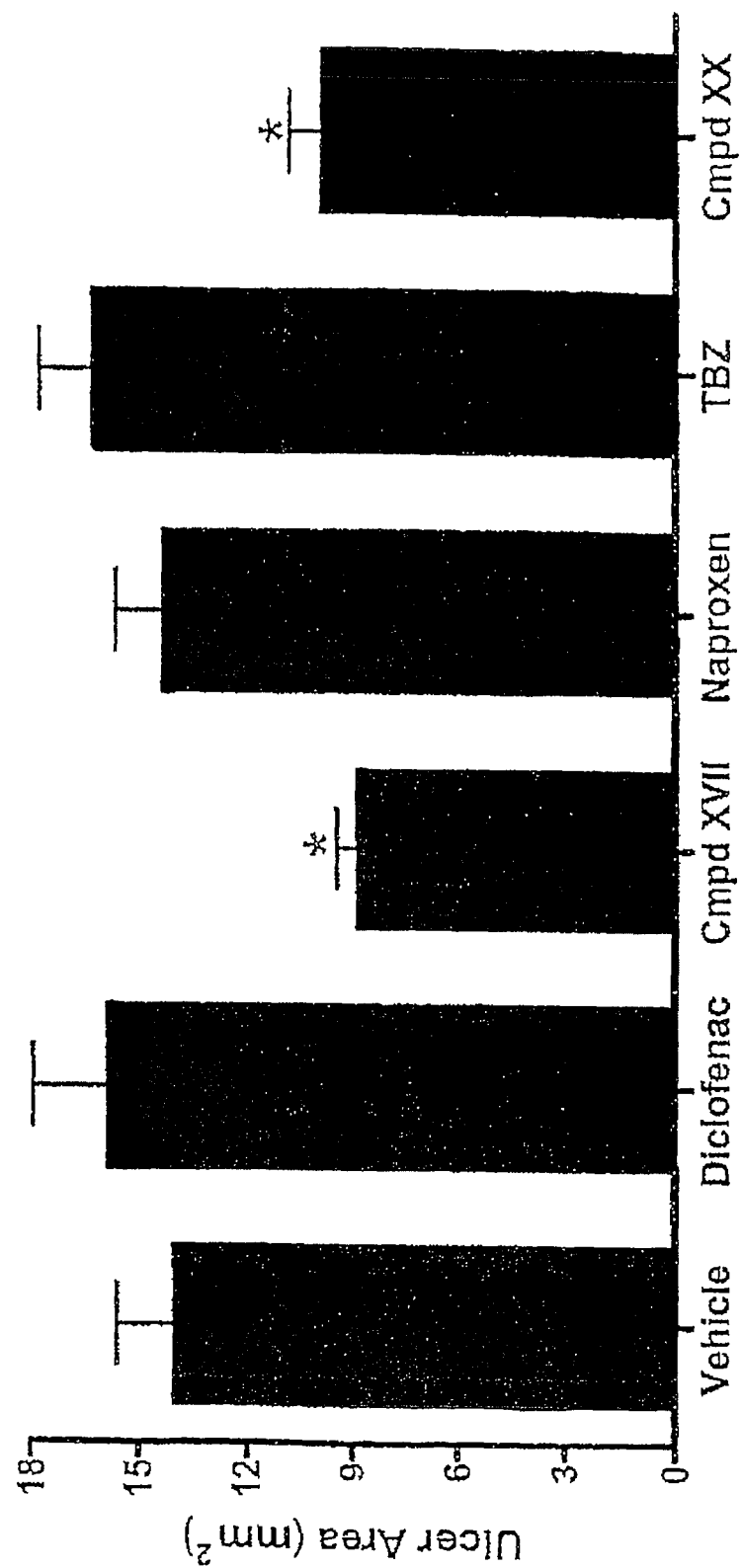
FIG. 13 illustrates the surface area, in $mm^2$, of gastric ulcers in the rat following daily treatment for one week with vehicle, diclofenac, Compound XVII, naproxen and Compound XX.

NSAIDs, including those selective for COX-2, often inhibit healing of pre-existing gastric ulcers (Stadler et al., *Diclofenac delays healing of gastroduodenal mucosal lesions. Double-blind, placebo-controlled endoscopic study in healthy volunteers*. Digestive Diseases and Sciences 1991; 36: 594-600). To determine the effects of two compounds of the present invention (Compound XVII and Compound XX), as compared to diclofenac and naproxen, respectively, on ulcer healing, rats were treated with these drugs after ulcers had been induced in their stomachs. Gastric ulcers were induced via serosal application of acetic acid, as described by Elliott et al., *A nitric oxide-releasing nonsteroidal anti-inflammatory drug accelerates gastric ulcer healing in rats*. Gastroenterology 1995; 109: 524-530. Beginning three days later, groups of 5 rats each were treated twice-daily, orally, with vehicle, diclofenac, (30 µmol/kg), Compound XVII (30 µmol/kg), naproxen (60 µmol/kg) or Compound XX (60 µmol/kg). After 4 days of such treatment, the rats were euthanized and the stomach was excised and photographed. The area (in $mm^2$) of the ulcer was determined planimetrically by an individual unaware of the treatments given to the rats. In a subgroup of 5 rats euthanized 3 days after induction of gastric ulcers (i.e., prior to initiation of drug treatment), the mean surface area of the ulcers was 24±2 $mm^2$. As illustrated in FIG. 13, rats treated with vehicle, diclofenac or naproxen exhibited similar degrees of healing. However, rats treated with Compound XVII or Compound XX exhibited significantly greater healing (*p<0.05 compared to diclofenac and naproxen, respectively). Treatment with the hydrogen sulfide releasing moiety of these two compounds (TBZ) did not significantly affect the healing of gastric ulcers as compared to the vehicle-treated group.

Example 23

Effects of Compounds of the Present Invention on Blood Pressure

Figure 14:
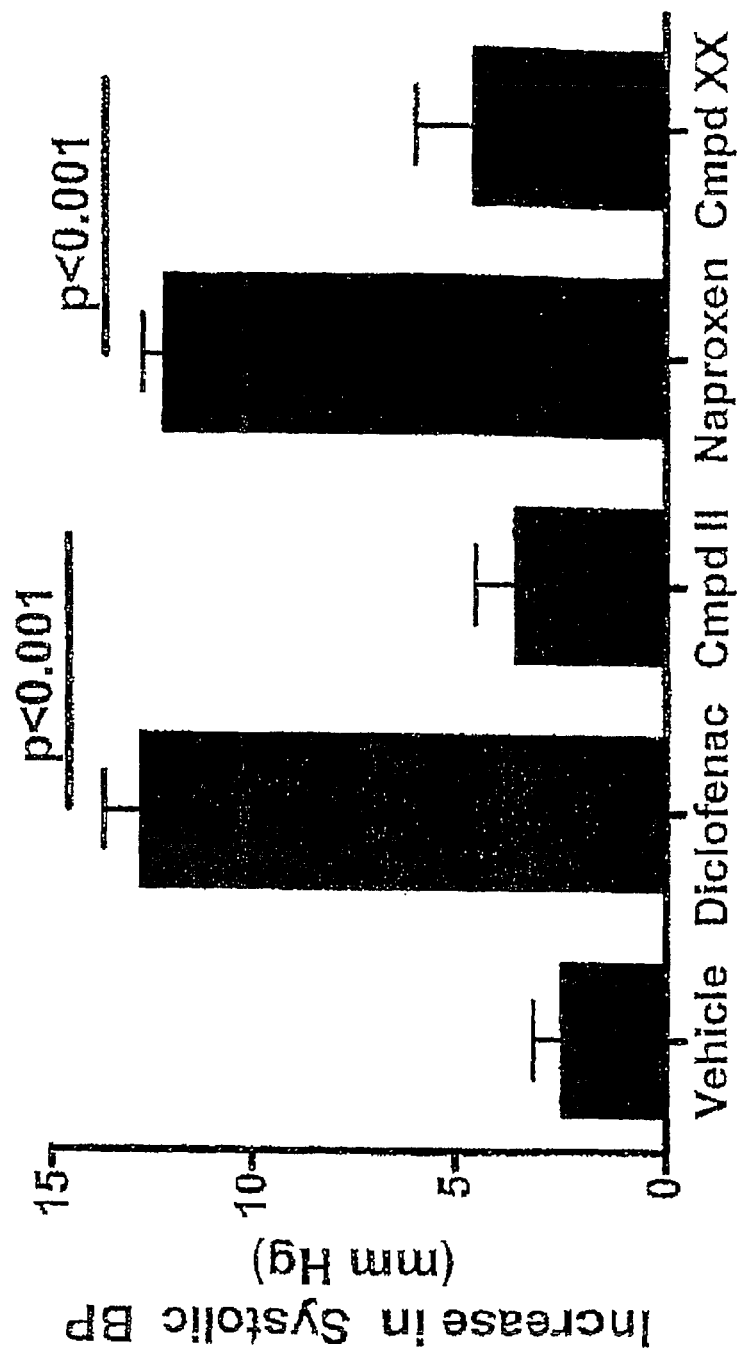
FIG. 14 illustrates the increase in systolic blood pressure (mm Hg) in rats treated with vehicle, diclofenac, Compound II, naproxen and Compound XX.

NSAIDs, including those exhibiting selectivity for COX-2, may exacerbate pre-existing hypertension and interfere with the effectiveness of some anti-hypertensive medications (Whelton, A. *Nephrotoxicity of nonsteroidal anti-inflamma-* tory drugs: physiologic foundations and clinical implications. Am. J. Med. 1999; 106 (5B): 13S-24S). To determine the effects of two compounds of the present invention (Compound II and Compound XX), as compared to diclofenac and naproxen, respectively, on blood pressure, rats given these drugs intraperitoneally after first inducing hypertension. The rats were provided with drinking water supplemented with Nω-nitro-L-arginine methylester (400 mg/L) for 7 days prior to the experiment, as described previously by Ribeiro et al. (*Chronic inhibition of nitric oxide synthesis: A new model or arterial hypertension.* Hypertension 1992; 20: 298-303). The rats (5 to 8 per group) were anesthetized with Halothane and a carotid artery was cannulated for measurement of blood pressure, which was recorded continuously on a chart recorder. After measuring a stable blood pressure for at least 15 minutes, one of the drugs (naproxen, diclofenac, Compound II or Compound XX) was injected intraperitoneally as a bolus (diclofenac and Compound II were administered at 30 μmol/kg while naproxen and Compound XX were administered at 60 μmol/kg). Changes in blood pressure were recorded for 60 minutes after the injection. The mean basal blood pressure was 150±6 mm Hg. FIG. 14 illustrates that diclofenac and naproxen caused a substantial increase in systolic blood pressure. In contrast, Compound II and Compound XX did not increase systolic blood pressure as compared to the vehicle-treated group, and the change in blood pressure was significantly lower than that induced by diclofenac and naproxen, respectively.

Example 24

Measurement of Plasma $H_2S$ Concentrations

To determine the kinetics of $H_2S$ released from Compound II, groups of 5 rats were treated with Compound II at the dose of 50 μmol/kg p.o. and sacrificed after 10, 30, 60 and 180 minutes. A time-course curve of plasma $H_2S$ concentrations was then constructed. Plasma $H_2S$ concentrations were measured as described previously (Ubuka, T. Assay methods and biological roles of labile sulfur in animal tissues. *J Chromatogr B Analyt Technol Biomed Life Sci.* 2002; 781: 227-249 and Zhao W, Zhang J, Lu Y, Wang R. The vasorelaxant effect of $H_2S$ as a novel endogenous gaseous K(ATP) channel opener. *EMBO J.* 2001; 20: 6008-6016, both of which are incorporated hereto by reference) with modifications. Briefly, 250 μl of plasma were added to ice-cold 250 μl of NaOH 0.1 N in a sealed 3-neck reactor. A constant stream of nitrogen was passed through the mixture via a gas-inlet capillary. The reactor was maintained at 37° C. and $H_2S$ extraction was started by introducing 1 ml of 10% trichloroacetic acid solution. The stream of nitrogen carried the sulfide acid in another reactor by cooled connector and bubbling in 2 ml of sulfide anti-oxidant buffer (SAOB) solution, consisting of 2 M KOH, 1 M salicylic acid and 0.22 M ascorbic acid at pH 12.8. After 30 minutes the SAOB solution was removed, and the sulfide concentration was measured with a sulfide sensitive electrode (Model 9616 $S^{2-}/Ag^+$ electrode, Orion Research, Beverly, Mass., USA) and expressed as $H_2S$ (Ubuka, 2002; Khan et al., 1980).

To compare the in vitro $H_2S$ release induced by Compound XVII and Compound II, and TBZ and ADT-OH, the $H_2S$ releasing moieties of Compound XVII and Compound II, respectively, 100-150 mg of isolated livers were homogenized in 1 ml of ice-cold T-PER protein extractor. The $H_2S$ release was lead on the same reactor of plasma analysis. Two ml of an assay reaction mixture was introduced in the reactor. The mixture contained 1 mM Compound II, 1 mM Compound XVII, 1 mM TBZ or 1 mM ADT-OH dissolved in PEG and 100 mM potassium phosphate buffer (pH=7.4). Incubations were lead with or without presence of 10% (w/v) liver homogenate and 2 mM pyridoxal 5'-phosphate. A constant stream of nitrogen was passed through the mixture via gas-inlet capillary. Reactions were initiated by transferring the tube from ice bath to a 37° C. water bath. The stream of nitrogen carried the sulfide acid in the second reactor containing 2 ml of SAOB as described previously. After incubating at 37° C. for 90 minutes, 1 ml of 50% trichloroacetic acid solution was added to mixture to stop the reaction. The remainder $H_2S$ in the mixture was carried out via nitrogen stream by other 30 minutes of incubation at 37° C. The concentration of sulfide in SAOB solution was measured with a sulfide sensitive electrode as previously described (Ubuka, 2002; Khan et al., 1980).

Figure 15:
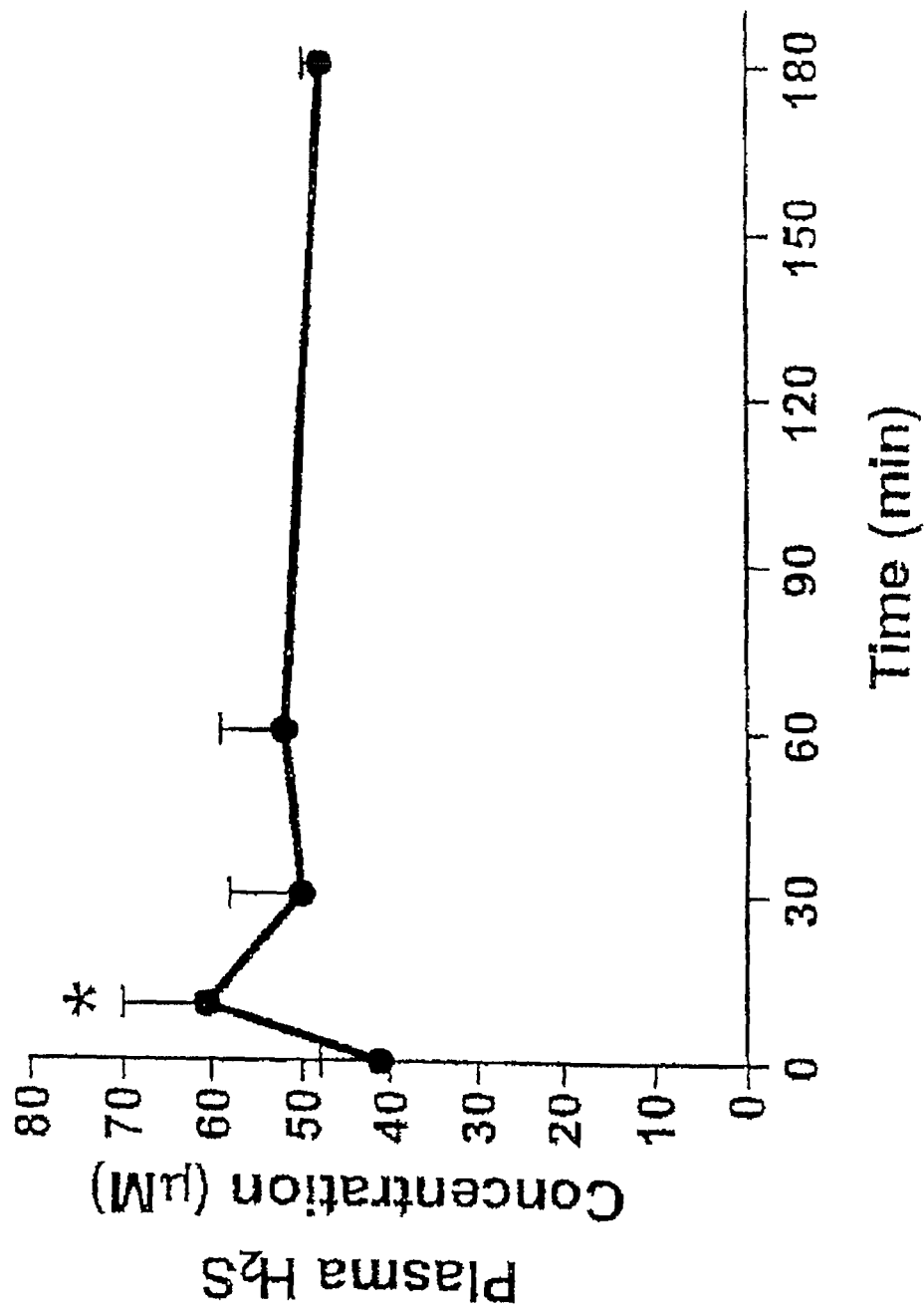
FIG. 15 illustrates the plasma hydrogen sulfide concentration when rats were treated with 50 µmol/kg p.o. of Compound II.
Figure 16:
FIG. 16 illustrates the amount of hydrogen sulfide generated from Compound II and Compound XVII when incubated in buffer and in liver homogenate.

As shown in FIG. 15, oral administration of Compound II resulted in a significant (p<0.05) increase in plasma levels of $H_2S$. A small but consistent increase in plasma $H_2S$ was observed for 180 minutes after the single administration of Compound II. FIG. 16 shows that incubation of Compound II or Compound XVII in buffer resulted in significantly more release of $H_2S$ than an equivalent amount of ADT-OH or TBZ, respectively. Similarly, there was greater release of $H_2S$ from Compound II and Compound XVII than from ADT-OH or TBZ when incubated with liver homogenate.

We claim:

1. A compound of the formula:

A—Y—X         (Formula I)

wherein A is an NSAID radical, Y is selected from the group consisting of —C(O)O—, —C(O)NH—, —C(O)OC(O)—, —C(O)NHCH$_2$C(O)—, or zero, and X is either

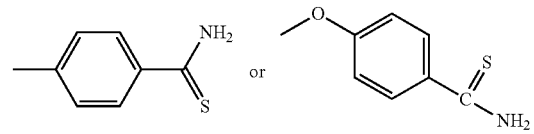

or a salt thereof;

whereby when Y is zero, the compound may be a salt of A and X.

2. A compound of the formula:

B—C(O)O—X         (Formula II)

where B—C(O)O— is derived from an NSAID having a free carboxyl group or a carboxy-substituted NSAID, and X is

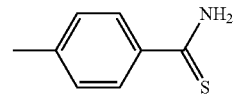

or a salt thereof.

3. The compound according to claim 1, wherein the NSAID is selected from the group consisting of acetylsalicylic acid (ASA), diclofenac, naproxen, indomethacin, flurbiprofen, sulindac, ibuprofen, aceclofenac, acemetacin, benoxaprofen, benzofenac, bromfenac, bucloxic acid, butibufen, carprofen, celecoxib, cicloprofen, cinmetacin, clidenac, clopirac, diflusinal, etodolac, etoricoxib, fenbufen, fenclofenac, fenclorac, fenoprofen, fentiazac, flunoxaprofen, furaprofen, furobufen, furafenac, ibufenac, indoprofen, isoxepac, ketoprofen, ketorolac, loxoprofen, lonazolac, lumiracoxib, metiazinic, mefenamic acid, meclofenamic acid, meloxicam, nabumetone, piromidic acid, salsalate, miroprofen, oxaprozin, oxepinac, paracoxib, phenylbutazone, pirprofen, piroxicam, pirozolac, protizinic acid, rofecoxib, sodium salicylate, suprofen, tiaprofenic acid, tolmetin, valdecoxib, and zomepirac.

4. The compound according to claim 2, wherein the NSAID is selected from the group consisting of acetylsalicylic acid, naproxen, indomethacin, flurbiprofen, ibuprofen, aceclofenac, acemetacin, benoxaprofen, benzofenac, bromfenac, bucloxic acid, butibufen, carprofen, celecoxib, cicloprofen, cinmetacin, clidenac, clopirac, etodolac, etoricoxib, fenbufen, fenclofenac, fenclorac, fenoprofen, fentiazac, flunoxaprofen, furaprofen, furobufen, furafenac, ibufenac, indoprofen, isoxepac, loxoprofen, lonazolac, lumiracoxib, metiazinic, mefenamic acid, meclofenamic acid, meloxicam, nabumetone, piromidic acid, salsalate, miroprofen, oxaprozin, oxepinac, paracoxib, phenylbutazone, pirprofen, piroxicam, pirozolac, protizinic acid, rofecoxib, sodium salicylate, suprofen, tiaprofenic acid, tolmetin, valdecoxib, and zomepirac.

5. The compound according to claim 1, wherein the NSAID is selected from the group consisting of acetylsalicylic acid, naproxen, indomethacin, flurbiprofen, ibuprofen, aceclofenac, acemetacin, benoxaprofen, benzofenac, bromfenac, bucloxic acid, butibufen, carprofen, cicloprofen, cinmetacin, clidenac, clopirac, fenbufen, fenclofenac, fenclorac, fenoprofen, fentiazac, flunoxaprofen, furaprofen, furobufen, furafenac, ibufenac, indoprofen, isoxepac, loxoprofen, lonazolac, lumiracoxib, metiazinic, mefenamic acid, nabumetone, piromidic acid, salsalate, miroprofen, oxaprozin, oxepinac, phenylbutazone, pirprofen, pirozolac, protizinic acid, suprofen, tiaprofenic acid, and tolmetin.

6. The compound according to claim 1, wherein the NSAID is selected from the group consisting of acetylsalicylic acid, diclofenac, indomethacin, lumiracoxib, naproxen, ibuprofen, ketoprofen and flurbiprofen; Y is —C(O)O—; and X is

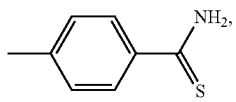

or a salt thereof.

7. Compound of claim 1 where the compound is

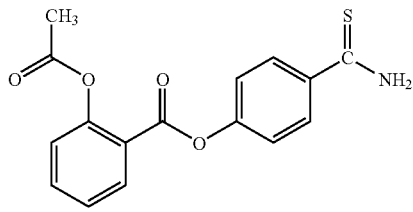

(XVI)

2-Acetoxy-benzoic acid 4-thiocarbamoyl-phenyl ester or a pharmaceutically acceptable salt thereof.

8. Compound of claim 1 where the compound is

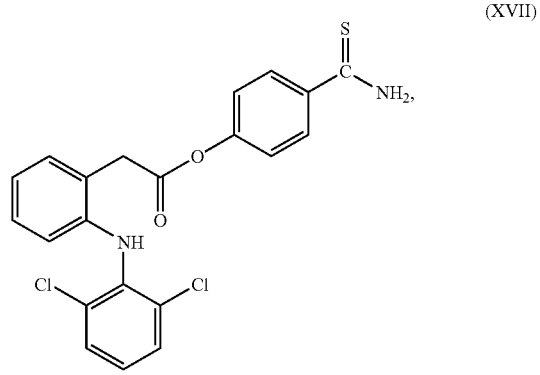

(XVII)

[2-(2,6-Dichloro-phenylamino)-phenyl]-acetic acid 4-thiocarbamoyl-phenyl ester or a pharmaceutically acceptable salt thereof.

9. Compound of claim 1 where the compound is

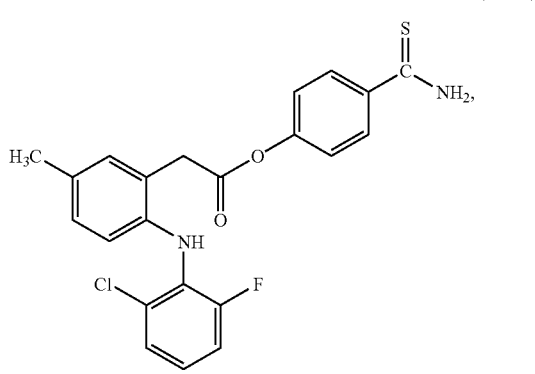

(XVIII)

[2-(2-Chloro-6-fluoro-phenylamino)-5-methyl-phenyl]-acetic acid 4-thiocarbamoyl-phenyl ester or a pharmaceutically acceptable salt thereof.

10. Compound of claim 1 where the compound is

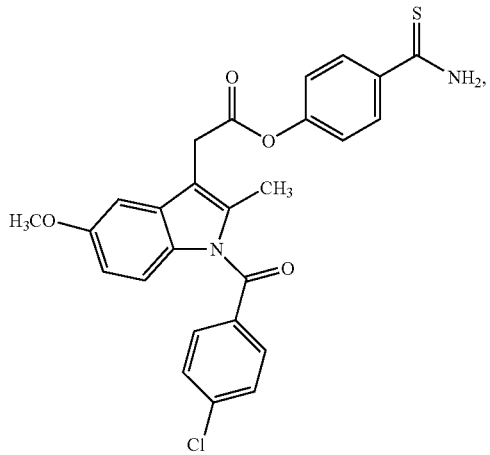

(XIX)

[1-(4-Chloro-benzoyl)-5-methoxy-2-methyl-1H-indol-3-yl]-acetic acid 4-thiocarbamoyl-phenyl ester or a pharmaceutically acceptable salt thereof.

11. Compound of claim 1 where the compound is

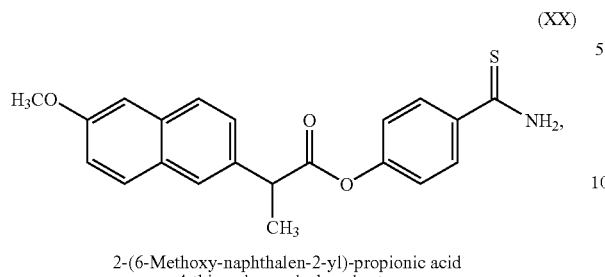

2-(6-Methoxy-naphthalen-2-yl)-propionic acid 4-thiocarbamoyl-phenyl ester (XX)

or a pharmaceutically acceptable salt thereof.

12. Compound of claim 1 where the compound is

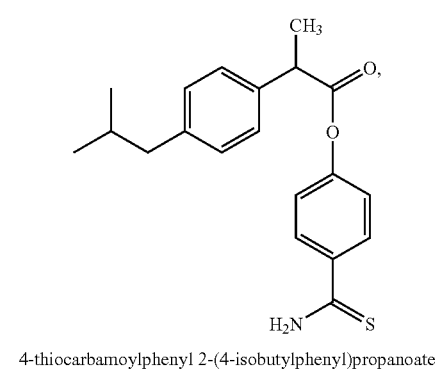

4-thiocarbamoylphenyl 2-(4-isobutylphenyl)propanoate (XXIX)

or a pharmaceutically acceptable salt thereof.

13. Compound of claim 1 where the compound is

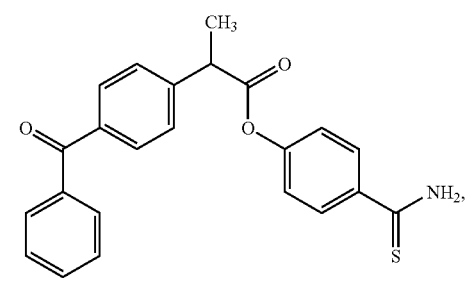

4-thiocarbamoylphenyl 2-(4-oxophenyl)-phenyl propanoate (XXX)

or a pharmaceutically acceptable salt thereof.

14. Compound of claim 1 where the compound is

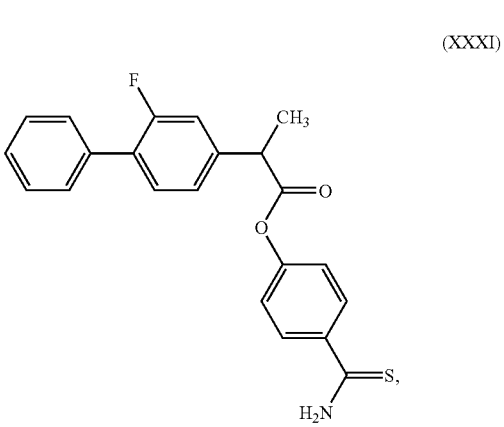

4-thiocarbamoylphenyl 2-(2-Fluoro-4-biphenylyl)propanoate (XXXI)

or a pharmaceutically acceptable salt thereof.

15. A pharmaceutical composition comprising a compound as claimed in claim 1 and a pharmaceutically acceptable excipient or carrier.

16. The compound according to claim 1, wherein the NSAID is selected from the group consisting of acetylsalicylic acid (ASA), naproxen, indomethacin, flurbiprofen, ibuprofen, aceclofenac, acemetacin, benoxaprofen, benzofenac, bromfenac, bucloxic acid, butibufen, carprofen, celecoxib, cicloprofen, cinmetacin, clidenac, clopirac, etodolac, etoricoxib, fenbufen, fenclofenac, fenclorac, fenoprofen, fentiazac, flunoxaprofen, furaprofen, furobufen, furafenmac, ibufenac, indoprofen, isoxepac, loxoprofen, lonazolac, lumiracoxib, metiazinic, mefenamic acid, meclofenamic acid, meloxicam, nabumetone, piromidic acid, salsalate, miroprofen, oxaprozin, oxepinac, paracoxib, phenylbutazone, pirprofen, piroxicam, pirozolac, protizinic acid, rofecoxib, sodium salicylate, suprofen, tiaprofenic acid, tolmetin, valdecoxib, and zomepirac.

17. The compound according to claim 2, wherein the NSAID is selected from the group consisting of acetylsalicylic acid, diclofenac, indomethacin, lumiracoxib, naproxen, ibuprofen, ketoprofen and flurbiprofen.

18. A pharmaceutical composition comprising a compound as claimed in claim 2 and a pharmaceutically acceptable excipient or carrier.

* * * * *